(12) United States Patent
Klingler et al.

(10) Patent No.: US 7,910,576 B2
(45) Date of Patent: Mar. 22, 2011

(54) PYRROLE DERIVATIVES AS P2Y12 ANTAGONISTS

(75) Inventors: Otmar Klingler, Frankfurt (DE); Joerg Czech, Marburg (DE); Werngard Czechtizky, Frankfurt (DE); Tilo Weiss, Frankfurt am Main (DE); Melitta Just, Langen (DE)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/639,500

(22) Filed: Dec. 16, 2009

(65) Prior Publication Data

US 2010/0226918 A1 Sep. 9, 2010

Related U.S. Application Data

(63) Continuation of application No. PCT/EP2008/004459, filed on Jun. 4, 2008.

(30) Foreign Application Priority Data

Jun. 18, 2007 (EP) .................................. 07290755

(51) Int. Cl.
*A61K 31/454* (2006.01)
*A61K 31/496* (2006.01)
*C07D 401/14* (2006.01)
*C07D 401/02* (2006.01)
*C07D 403/14* (2006.01)
*C07D 403/02* (2006.01)

(52) U.S. Cl. .............. 514/217.08; 514/254.01; 546/208; 544/364; 544/372

(58) Field of Classification Search .................. None
See application file for complete search history.

(56) References Cited

U.S. PATENT DOCUMENTS

| | | | |
|---|---|---|---|
| 3,458,515 A | 7/1969 | Archibald et al. | |
| 2002/0061892 A1 | 5/2002 | Wang et al. | |
| 2003/0119817 A1 | 6/2003 | Mehta et al. | |
| 2006/0148806 A1 | 7/2006 | Watanuki et al. | |

FOREIGN PATENT DOCUMENTS

| | | |
|---|---|---|
| CN | 01778801 | 5/2006 |
| WO | WO 02/098856 A2 | 12/2002 |
| WO | WO 2004/052366 A1 | 6/2004 |
| WO | WO 2005/009971 A1 | 2/2005 |
| WO | WO 2005/073203 | 8/2005 |
| WO | WO 2006/077851 A1 | 7/2006 |
| WO | WO 2007/103456 | 9/2007 |

OTHER PUBLICATIONS

Takasaki et al, Molecular Cloning of the Platelet P2TAC ADP Receptor: Pharmacological Comparison with Another ADP Receptor, the P2Y1 Receptor, Mol. Pharmacol. 2001 (60) pp. 432-439.
Andre et al, P2Y12 regulates platelet adhesion/activation, thrombus growth, and thrombus stability in injhured arteries, J Clin. Inv. 2003 (112) 3 pp. 398-406.
Dangelmaier et al, Potentiation of Thromboxane A2-induced Platelet Secretion by Gi Signaling through the Phosphoinositide-3 Kinase Pathway, Thromb. Haemost. 2001 (85) pp. 341-348.
Gachet, ADP Receptors of Platelets and their Inhibition, Thromb. Haemost. 2001 (86) pp. 222-232.
Herbert et al, Inhibitory Effect of Clopidogrel on Platelet Adhesion and Intimal Proliferation After Arterial Injury in Rabbits, Arteroscl. and Thromb. 1993 (13) 9 pp. 1171-1179.
Khanna Ish K et al., 1,2-Diarylimidazoles as Potent, Cyclooxygenase-2 Selective, and Orally Active Antiinflammatory Agents, J. Med. Chem., 1997, vol. 40, pp. 1634-1647.
Kunapuli et al, ADP Receptors-Targets for Developing Antithrombotic Agents, Current Pharma. Design, 2003 (9) pp. 2303-2316.
Maffrand et al, ADP Plays a Key Role in Thrombogenesis in Rats, Thrombosis and Haemostasis 1988 (59) 2 pp. 225-230.
Savi et al, Identification and Biological Activity of the Active Metabolite of Clopidogrel, Thromb. Haemost. 2000 (84) pp. 891-896.
Stetter, Die katalysierte Addition von Aldehyden an aktivierte Doppelbindungen—1in neues Syntheseprinzip Angew. Chemie 1976 (21) pp. 695-736.
Storey, The P2Y12 receptor as a therapeutic target in cardiovascular disease, Platelets, 2001 (12) pp. 197-209.

*Primary Examiner* — Yong Chu
*Assistant Examiner* — Michael Barker
(74) *Attorney, Agent, or Firm* — Ronald G. Ort; Scully, Scott, Murphy and Presser, P.C.

(57) ABSTRACT

The present invention relates to compounds of the formula I,

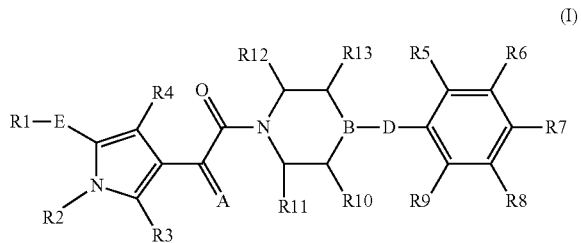

(I)

in which R1; R2; R3; R4; R5; R6; R7; R8; R9; R10; R11; R12; R13; A; B, D and E have the meanings indicated in the claims. The compounds of the formula I are valuable pharmacologically active compounds. They exhibit a strong anti-aggregating effect on platelets and thus an anti-thrombotic effect and are suitable e.g. for the therapy and prophylaxis of cardio-vascular disorders like thromboembolic diseases or restenoses. They are reversible antagonists of the platelet ADP receptor P2Y12, and can in general be applied in conditions in which an undesired activation of the platelet ADP receptor P2Y12 is present or for the cure or prevention of which an inhibition of the platelet ADP receptor P2Y12 is intended. The invention furthermore relates to processes for the preparation of compounds of the formula I, their use, in particular as active ingredients in pharmaceuticals, and pharmaceutical preparations comprising them.

8 Claims, No Drawings

PYRROLE DERIVATIVES AS P2Y12 ANTAGONISTS

FIELD OF THE INVENTION

The present invention relates to compounds of the formula I,

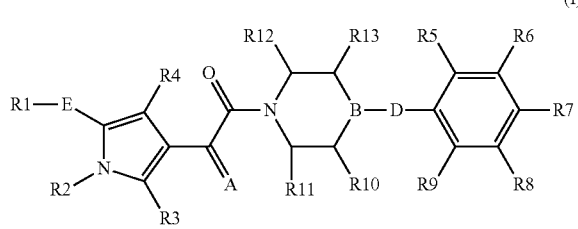

in which R1; R2; R3; R4; R5; R6; R7; R8; R9; R10; R11; R12; R13; A; B, D and E have the meanings indicated below. The compounds of the formula I are valuable pharmacologically active compounds. They exhibit a strong anti-aggregating effect on platelets and thus an anti-thrombotic effect and are suitable e.g. for the therapy and prophylaxis of cardiovascular disorders like thromboembolic diseases or restenoses. They are reversible antagonists of the platelet ADP receptor P2Y12, and can in general be applied in conditions in which an undesired activation of the platelet ADP receptor P2Y12 is present or for the cure or prevention of which an inhibition of the platelet ADP receptor P2Y12 is intended. The invention furthermore relates to processes for the preparation of compounds of the formula I, their use, in particular as active ingredients in pharmaceuticals, and pharmaceutical preparations comprising them.

BACKGROUND OF THE INVENTION

In the industrialized world thrombotic complications are one of the major causes of death. Examples of conditions associated with pathological thrombus formation include deep vein thrombosis, venous and arterial thromboembolism, thrombophlebitis, coronary and cerebral arterial thrombosis, cerebral embolism, renal embolism and pulmonary embolism, disseminated intravascular coagulation, transient ischemic attacks, strokes, acute myocardial infarction, unstable angina, chronic stable angina, peripheral vascular disease, preeclampsia/eclampsia, and thrombotic cytopenic purpura. Also during or following invasive procedures, including insertion of endovascular devices and protheses, carotid endarterectomy, angioplasty, CABG (coronary artery bypass graft) surgery, vascular graft surgery, and stent placements, thrombotic and restenotic complications could occur.

Platelet adhesion and aggregation play a critical role in these intravascular thrombotic events. Platelets can be activated by mediators released from circulating cells and damaged endothelial cells lining the vessel or by exposed subendothelial matrix molecules such as collagen, or by thrombin, which is formed in the coagulation cascade. Furthermore platelets can be activated under conditions of high shear blood flow in diseased vessels. Following activation, platelets, which normally circulate freely in the vasculature and other cells, accumulate at the site of a vessel injury to form a thrombus and recruit more platelets to the developing thrombus. During this process, thrombi can grow to a sufficient size to partly or completely block arterial blood vessels.

In veins thrombi can also form in areas of stasis or slow blood flow. These venous thrombi can create emboli that travel through the circulatory system, as they easily detach portions of themselves. These traveling emboli can block other vessels, such as pulmonary or coronary arteries, which can result in the above mentioned pathological outcomes such as pulmonary or coronary embolism.

In summary, for venous thrombi, morbidity and mortality arise primarily after embolization or distant blockade of vessels, whereas arterial thrombi cause serious pathological conditions by local blockade.

It was demonstrated by many studies that ADP (adenosine 5'-diphosphate) is an important mediator of platelet activation and aggregation. It therefore plays a key role in the initiation and progression of arterial thrombus formation (Maffrand, et al., Thromb. Haemostas. (1988); 59: 225-230; Herbert, et al., Arterioscl. Thromb. (1993), 13: 1171-1179).

Upon activation by various agents, such as collagen and thrombin, ADP is released from blood platelets in the vasculature, as well as from damaged blood cells, endothelium or tissues. The ADP-induced platelet aggregation is triggered by its binding to two specific G protein-coupled receptors expressed on the plasma membrane of human platelets: $P2Y_1$, and $P2Y_{12}$. ADP binding to these receptors induces inhibition of adenylyl cyclase and modulation of intracellular signaling pathways such as influx and mobilization of intracellular $Ca^{2+}$, activation of phosphoinositide-3 kinase (PI3K), shape change, secretion of other mediators, and platelet aggregation (Dangelmaier, et al. Thromb. Haemost. (2001), 85: 341-348). Activation by ADP results in the recruitment of more platelets and stabilization of existing platelet aggregates. Activation of the $P2Y_1$ receptor leads to calcium mobilization from intracellular stores, platelet shape change and initiation of aggregation.

Activation of the $P2Y_{12}$ receptor (also referred to as HORK3, P2RY12, SP1999, P2TAC, or P2YAC) by ADP, leads to inhibition of adenylyl cyclase and activation of PI3K. Activation of $P2Y_{12}$ is required for platelet secretion and stabilization of platelet aggregates (Gachet, Thromb. Haemost. (2001), 86, 222-232; Andre, et al., J. Clin. Invest., (2003), 112, 398-406). There are several reports about directly or indirectly acting synthetic inhibitors of ADP-dependent platelet aggregation which show antithrombotic activity.

The orally active thienopyridines, ticlopidine and clopidogrel, react covalently with the $P2Y_{12}$ receptor and lead to an irreversible platelet inhibition in vivo. They also inhibit binding of radiolabeled ADP receptor agonist 2-methylthioadenosine 5'-diphosphate to platelets, and other ADP-dependent events (Savi, et al., Thromb Haemost. (2000), 84: 891-896).

Bryant et al. (WO 2002/098856 and WO2004/052366) disclose quinoline derivatives, useful as antithrombotic agents via inhibition of the platelet ADP receptor. Watanuki et al. WO2005/009971 and Koga et al. WO2006/077851 disclose quinolone derivatives and 4-quinolone-3-carboxamide derivatives as P2Y12 inhibitors However, besides being effective P2Y12 antagonists, which antagonize the effect of endogenous ADP on its platelet ADP receptor, it is desirable that such antagonists also have further advantageous properties, for instance stability in plasma and liver and selectivity versus other receptors whose agonism or antagonism is not intended. There is an ongoing need for further low molecular weight P2Y12 antagonist, which are effective and have the above advantages as well.

DESCRIPTION OF THE INVENTION

The present invention satisfies the above needs by providing novel compounds of the formula I, which exhibit better P2Y12 antagonistic activity and are favorable agents with high bioavailability.

Thus, the present invention relates to compounds of formula I,

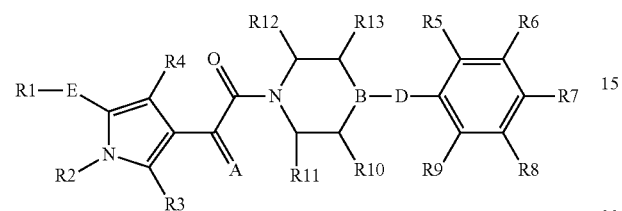

(I)

wherein
R1 is
1) hydrogen atom,
2) —($C_1$-$C_8$)-alkyl,
3) —($C_0$-$C_4$)-alkylene-($C_3$-$C_8$)-cycloalkyl, wherein cycloalkyl is unsubstituted or mono-, di- or trisubstituted independently of one another by halogen,
4) —($C_0$-$C_4$)-alkylene-($C_6$-$C_{14}$)-aryl, and wherein aryl is unsubstituted or mono-, di- or trisubstituted independently of one another by R15, or
5) —($C_0$-$C_4$)-alkylene-heterocyclyl, wherein heterocyclyl is mono or bicyclic and contains 3 to 15 ring carbon atoms and wherein one or more of the ring carbon atoms are replaced by 1, 2, 3 or 4 heteroatoms chosen from nitrogen, sulfur or oxygen, and wherein said heterocyclyl is unsubstituted or mono-, di- or trisubstituted independently of one another by R14;

E is
1) a covalent bond,
2) —NH—C(O)— or
3) —O—C(O)—,

R2 is
1) hydrogen atom or
2) —($C_1$-$C_8$)-alkyl,

R3 is
1) —($C_1$-$C_8$)-alkyl,
2) —$CF_3$, or
3) —($C_1$-$C_8$)-alkylene-C(O)—O—R16, R4 is
1) hydrogen atom,
2) —($C_1$-$C_8$)-alkyl,
3) —($C_1$-$C_8$)-alkylene-C(O)—O—R16,
4) —($C_2$-$C_6$)-alkenylene-C(O)—O—R16,
5) —($C_3$-$C_8$)-cycloalkyl-C(O)—O—R16, or
6) halogen, A is selected from oxygen atom or N—OH,
B is selected from nitrogen atom or CH,
D is
1) a covalent bond,
2) —C(O)— or
3) —$CH_2$—, R5, R6, R7, R8 and R9 are independently of one another selected from
1) hydrogen atom,
2) —($C_1$-$C_8$)-alkyl, wherein alkyl is unsubstituted or mono-, di- or trisubstituted independently of one another by halogen,
3) —($C_0$-$C_4$)-alkylene-O—R16,
4) halogen,
5) —($C_0$-$C_4$)-alkylene-O—($C_1$-$C_8$)-alkylene-O—R16,
6) —$NO_2$,
7) —CN,
8) —($C_0$-$C_4$)-alkylene-N(R16)-R17,
9) —($C_0$-$C_4$)-alkylene-C(O)—R16,
10) —($C_0$-$C_4$)-alkylene-C(O)—O—R16,
11) —($C_0$-$C_4$)-alkylene-C(O)—N(R16)-R17,
12) —O—($C_0$-$C_4$)-alkylene-C(O)—O—R16,
13) —O—($C_0$-$C_4$)-alkylene-C(O)—N(R16)-R17
14) —($C_0$-$C_4$)-alkylene-($C_3$-$C_{15}$)-heterocyclyl, wherein heterocyclyl is un-substituted or mono-, di- or trisubstituted independently of one another by R14, or
15) —O—($C_0$-$C_4$)-alkylene-($C_3$-$C_{15}$)-heterocyclyl, wherein heterocyclyl is un-substituted or mono-, di- or trisubstituted independently of one another by R14, or R5 and R6 or R6 and R7 form together with the atoms which they are attached to a 5-, 6- or 7-membered carbon ring, wherein said carbon ring is aromatic, partially unsaturated or saturated, or in which one, two or three of the 5 to 7 ring carbon atoms are replaced by heteroatoms such as nitrogen, oxygen or sulfur, and wherein said carbon ring is unsubstituted or substituted one, two, three or four times by R15, R10, R11, R12 and R13 are independently of one another selected from
1) hydrogen atom,
2) —($C_1$-$C_8$)-alkyl,
3) =O or
4) —OH, R14 is halogen, —OH, =O, —($C_1$-$C_8$)-alkyl, —O—($C_1$-$C_8$)-alkyl, —$CF_3$, —O—$CF_3$, —$NO_2$, —CN or —$NH_2$, R15 is halogen, —OH, —($C_1$-$C_8$)-alkyl, —O—($C_1$-$C_8$)-alkyl, —$CF_3$, —O—$CF_3$, —$NO_2$, —CN, —C(O)OH, —C(O)O—($C_1$-$C_8$)-alkyl, —C(O)$NH_2$ or —$NH_2$, R16 is hydrogen atom, —($C_1$-$C_8$)-alkyl or —($C_0$-$C_4$)-alkylene-($C_3$-$C_8$)-cycloalkyl, R17 is hydrogen atom or —($C_1$-$C_8$)-alkyl, or R17 and R16 form together with the nitrogen atom to which they are attached a 5-, 6- or 7-membered carbon ring, wherein said carbon ring is unsaturated or saturated, or in which one, two or three of the 5 to 7 ring carbon atoms are replaced by heteroatoms such as nitrogen, oxygen or sulfur, and wherein said carbon ring is unsubstituted or substituted one, two, three or four times by R15, in all their stereoisomeric forms and mixtures thereof in any ratio, and their physiologically tolerable salts.

2) The present invention also relates to compounds of the formula I, wherein
R1 is
1) —($C_1$-$C_8$)-alkyl,
2) —($C_0$-$C_4$)-alkylene-($C_3$-$C_8$)-cycloalkyl, wherein cycloalkyl is selected from cyclopropyl, cyclobutyl, cyclopentyl, cyclohexyl, cyloheptyl or cyclooctyl and is unsubstituted or mono-, di- or trisubstituted independently of one another by halogen,
3) —($C_0$-$C_4$)-alkylene-($C_6$-$C_{14}$)-aryl, and wherein aryl is selected from phenyl, naphthyl, biphenylyl, indanyl, anthryl or fluorenyl and is unsubstituted or mono-, di- or trisubstituted independently of one another by R15, or
4) —($C_0$-$C_4$)-alkylene-heterocyclyl, wherein heterocyclyl is selected from acridinyl, 8-aza-bicyclo[3.2.1]oct-3-yl, azaindole (1H-pyrrolopyridinyl), azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, and is unsubstituted or mono-, di- or trisubstituted independently of one another by R14;

E is
1) a covalent bond,
2) —NH—C(O)— or
3) —O—C(O)—,

R2 is
1) hydrogen atom or
2) —($C_1$-$C_8$)-alkyl,

R3 is
1) —($C_1$-$C_8$)-alkyl, or
2) —($C_1$-$C_8$)-alkylene-C(O)—O—R16,

R4 is
1) hydrogen atom,
2) —($C_2$-$C_6$)-alkenylene-C(O)—O—R16,
3) —($C_1$-$C_8$)-alkyl or
4) halogen, A is selected from oxygen atom or N—OH,
B is selected from nitrogen atom or CH,
D is
1) a covalent bond,
2) —C(O)— or
3) —CH$_2$—, R5, R6, R7, R8 and R9 are independently of one another selected from
1) hydrogen atom,
2) —($C_1$-$C_8$)-alkyl,
3) —($C_0$-$C_4$)-alkylene-O—R16,
4) halogen,
5) —($C_0$-$C_4$)-alkylene-O—($C_1$-$C_8$)-alkylene-O—R16,
6) —NO$_2$,
7) —CN,
8) —($C_0$-$C_4$)-alkylene-N(R16)-R17,
9) —($C_0$-$C_4$)-alkylene-C(O)—R16,
10) —($C_0$-$C_4$)-alkylene-C(O)—O—R16,
11) —($C_0$-$C_4$)-alkylene-C(O)—N(R16)-R17,
12) —O—($C_0$-$C_4$)-alkylene-C(O)—O—R16,
13) —O—($C_0$-$C_4$)-alkylene-C(O)—N(R16)-R17
14) —($C_0$-$C_4$)-alkylene-($C_3$-$C_{15}$)-heterocyclyl, wherein heterocyclyl is as defined above and is un-substituted or mono-, di- or trisubstituted independently of one another by R14, or
15) —O—($C_0$-$C_4$)-alkylene-($C_3$-$C_{15}$)-heterocyclyl, wherein heterocyclyl is as defined above and is un-substituted or mono-, di- or trisubstituted independently of one another by R14, or R5 and R6 or R6 and R7 form together with the atoms which they are attached to a 5-, 6- or 7-membered carbon ring selected from cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, cycloheptenyl, cyclohepta-1,3-dienyl, cyclohepta-1,4-dienyl, cyclohepta-1,3,5-trienyl, phenyl, 1,4 diazepane, 1,2-diazepine, 1,3-diazepine, 1,4-diazepine, diaziridine, diazirine, dihydroimidazolone, dioxazole, dioxazine, 1,4-dioxine, dioxole, 1,3-dioxolene, 1,3-dioxolane, furan, imidazole, imidazoline, imidazolidine, imidazolidinone, isothiazole, isothiazolidine, isothiazoline, isoxazole, isoxazoline, isoxazolidine, morpholine, 1,2-oxa-thiepane, 1,2-oxathiolane, 1,4-oxazepane, 1,2-oxazine, 1,3-oxazine, 1,4-oxazine, oxazolone, oxazole, [1,3,4]oxathiazinane 3,3-dioxide, oxaziridine, oxazolidinone, oxetan, oxirane, piperazine, piperidine, pyran, pyrazine, pyrazole, pyrazoline, pyrazolidine, pyridazine, pyridine, pyridinone, pyrimidine, pyrimidine-2,4-dione, pyrrole, pyrrolidine, pyrrolidinone, pyrroline, tetrahydrofuran, tetrahydropyran, tetrahydropyridine, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiomorpholine 1,1-dioxide thiopyran, 1,2,3-triazine, 1,2,4-triazine, 1,3,5-triazine, 1,2,3-triazole or 1,2,4-triazole, and wherein said carbon ring is unsubstituted or substituted one, two, three or four times by R15, R10, R11, R12 and R13 are independently of one another selected from
1) hydrogen atom,
2) —($C_1$-$C_8$)-alkyl or
3) —OH, R14 is halogen, —OH, =O, —($C_1$-$C_8$)-alkyl, —O—($C_1$-$C_8$)-alkyl, —CF$_3$, —O—CF$_3$, —NO$_2$, —CN or —NH$_2$,
R15 is halogen, —OH, —($C_1$-$C_8$)-alkyl, —O—($C_1$-$C_8$)-alkyl, —CF$_3$, —O—CF$_3$, —NO$_2$, —CN or —NH$_2$,
R16 is hydrogen atom or —($C_1$-$C_8$)-alkyl,
R17 is hydrogen atom or —($C_1$-$C_8$)-alkyl, in all their stereoisomeric forms and mixtures thereof in any ratio, and their physiologically tolerable salts.

3) The present invention also relates to compounds of the formula I, wherein
R1 is
1) —($C_1$-$C_4$)-alkyl,
2) —($C_0$-$C_2$)-alkylene-($C_3$-$C_6$)-cycloalkyl, wherein cycloalkyl is selected from cyclopropyl, cyclobutyl, cyclopentyl or cyclohexyl,
3) —($C_0$-$C_2$)-alkylene-phenyl, or 4) —(C₀-C₂)-alkylene-heterocyclyl, wherein heterocyclyl is selected from furanyl, pyridyl or tetrahydropyranyl, E is
1) a covalent bond,
2) —NH—C(O)— or
3) —O—C(O)—, R2 is hydrogen atom, R3 is
1) —(C₁-C₄)-alkyl, or
2) —(C₁-C₄)-alkylene-C(O)—O—R16, R4 is
1) hydrogen atom,
2) -ethenylene-C(O)—O—R16, or
3) —(C₁-C₄)-alkyl, A is selected from oxygen atom or N—OH, B is selected from nitrogen atom or CH, D is
1) a covalent bond,
2) —C(O)— or
3) —CH₂—, R5, R6, R7, R8 and R9 are independently of one another selected from
1) hydrogen atom,
2) —(C₁-C₄)-alkyl,
3) —O—R16,
4) chlorine,
5) fluorine,
6) —O—(C₁-C₄)-alkylene-O—R16,
7) —NO₂,
8) —CN,
9) —NH₂,
10) —C(O)—R16,
11) —C(O)—O—R16,
12) —(C₀-C₄)-alkylene-C(O)—N(R16)-R17,
13) —O—(C₁-C₄)-alkylene-C(O)—O—R16,
14) —O—(C₁-C₄)-alkylene-C(O)—N(R16)-R17, or
15) —O—(C₁-C₄)-alkylene-piperidinyl, or R5 and R6 or R6 and R7 form together with the atoms which they are attached to a ring selected from 1,4-dioxine or pyrrole, R10, R11, R12 and R13 are independently of one another selected from
1) hydrogen atom or
2) —(C₁-C₄)-alkyl, R16 is hydrogen atom or —(C₁-C₄)-alkyl, and R17 is hydrogen atom or —(C₁-C₄)-alkyl, in all their stereoisomeric forms and mixtures thereof in any ratio, and their physiologically tolerable salts.

4) The present invention also relates to compounds of the formula I, wherein

R1 is -phenyl,

E is a covalent bond,

R2 is hydrogen atom,

R3 is
1) —(C₁-C₄)-alkyl, or
2) —(C₁-C₄)-alkylene-C(O)—O—R16,

R4 is
1) hydrogen atom or
2) -ethenylene-C(O)—O—R16,
3) —(C₁-C₄)-alkyl,

A is oxygen atom,

B is nitrogen atom,

D is a covalent bond,

R5, R6, R7, R8 and R9 are independently of one another selected from
1) hydrogen atom,
2) —(C₁-C₄)-alkyl,
3) —O—R16,
4) chlorine,
5) fluorine,
6) —O—(C₁-C₄)-alkylene-O—R16,
7) —NO₂,
8) —CN,
9) —NH₂,
10) —C(O)—R16,
11) —C(O)—O—R16,
12) —(C₀-C₄)-alkylene-C(O)—N(R16)-R17,
13) —O—(C₁-C₄)-alkylene-C(O)—O—R16,
14) —O—(C₁-C₄)-alkylene-C(O)—N(R16)-R17 or
15) —O—(C₁-C₄)-alkylene-piperidinyl, or R5 and R6 or R6 and R7 form together with the atoms which they are attached to a ring selected from 1,4-dioxine or pyrrole, R10, R11, R12 and R13 are each a hydrogen atom, R16 is hydrogen atom or —(C₁-C₄)-alkyl, and R17 is hydrogen atom or —(C₁-C₄)-alkyl, in all their stereoisomeric forms and mixtures thereof in any ratio, and their physiologically tolerable salts.

As used herein, the term alkyl is a hydrocarbon residue, which can be linear, e.g. straight-chain, or branched. Examples of "—(C₁-C₈)-alkyl" or "—(C₁-C₈)-alkylene" are alkyl residues containing 1, 2, 3, 4, 5, 6, 7 or 8 carbon atoms are methyl, methylene, ethyl, ethylene, propyl, propylene, butyl, butylene, pentyl, pentylene, hexyl, hexylene, heptyl or octyl, the n-isomers of all these residues, isopropyl, isobutyl, 1-methylbutyl, isopentyl, neopentyl, 2,2-dimethylbutyl, 2-methylpentyl, 3-methylpentyl, isohexyl, secondary-butyl, tertiary-butyl, or tertiary-pentyl. The terms "—(C₀-C₈)-alkyl" or "—(C₀-C₈)-alkylene" are each hydrocarbon residues containing 1, 2, 3, 4, 5, 6, 7 or 8 carbon atoms. The terms "—C₀-alkyl" or "—C₀-alkylene" are understood as meaning each a covalent bond.

The term "—(C₂-C₆)-alkenylene" is understood as meaning an alkyl residue containing 1, 2, 3, 4, 5 or 6 carbon atoms and 1 or 2 double bonds such as vinylene (ethenylene, which is —CH=CH—), 1-propenylene, 2-propenylene (=allyl), 2-butenylene, 3-butenylene, 2-methyl-2-butenylene, 3-methyl-2-butenylene, 5-hexenylene or 1,3-pentadienylene.

The term "—(C₃-C₈)-cycloalkyl" is understood as meaning cycloalkyl residues containing 3, 4, 5, 6, 7 or 8 ring carbon atoms like cyclopropyl, cyclobutyl, cyclopentyl, cyclohexyl, cyloheptyl or cyclooctyl.

The terms "6- to 14-membered aryl" or "—(C₆-C₁₄)-aryl" are understood as meaning a mono- or bicyclic-aromatic hydrocarbon radicals containing from 6 to 14 carbon atoms in the ring. Examples are phenyl, naphthyl, for example 1-naphthyl and 2-naphthyl, biphenylyl, for example 2-biphenylyl, 3-biphenylyl and 4-biphenylyl, indanyl, anthryl or fluorenyl. Biphenylyl radicals, naphthyl radicals and, in particular, phenyl radicals are preferred aryl radicals.

The terms "mono- or bicyclic 3- to 15-membered heterocyclyl" or "—(C₃-C₁₅)-heterocyclyl" refer to heterocycles in which one or more of the 3 to 15 ring carbon atoms are replaced by heteroatoms such as nitrogen, oxygen or sulfur such as acridinyl, 8-aza-bicyclo[3.2.1]oct-3-yl, azaindole (1H-pyrrolopyridinyl), azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl.

The term "=O" refers to residues such as carbonyl (—C(O)—) or nitroso (—N=O).

Halogen is fluorine, chlorine, bromine or iodine, preferably fluorine, chlorine or bromine, particularly preferably chlorine or bromine.

The term "R5 and R6 or R6 and R7 form together with the atoms which they are attached to a 5-, 6- or 7-membered carbon ring, wherein said carbon ring is aromatic, partially unsaturated or saturated, or in which one, two or three of the 5 to 7 ring carbon atoms are replaced by heteroatoms such as nitrogen, oxygen or sulfur" refers to residues such as cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, cycloheptenyl, cyclohepta-1,3-dienyl, cyclohepta-1,4-dienyl, cyclohepta-1,3,5-trienyl, phenyl, 1,4 diazepane, 1,2-diazepine, 1,3-diazepine, 1,4-diazepine, diaziridine, diazirine, dihydroimidazolone, dioxazole, dioxazine, 1,4-dioxine, dioxole, 1,3-dioxolene, 1,3-dioxolane, furan, imidazole, imidazoline, imidazolidine, imidazolidinone, isothiazole, isothiazolidine, isothiazoline, isoxazole, isoxazoline, isoxazolidine, morpholine, 1,2-oxa-thiepane, 1,2-oxathiolane, 1,4-oxazepane, 1,2-oxazine, 1,3-oxazine, 1,4-oxazine, oxazolone, oxazole, [1,3,4]oxathiazinane 3,3-dioxide, oxaziridine, oxazolidinone, oxetan, oxirane, piperazine, piperidine, pyran, pyrazine, pyrazole, pyrazoline, pyrazolidine, pyridazine, pyridine, pyridinone, pyrimidine, pyrimidine-2,4-dione, pyrrole, pyrrolidine, pyrrolidinone, pyrroline, tetrahydrofuran, tetrahydropyran, tetrahydropyridine, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiomorpholine 1,1-dioxide thiopyran, 1,2,3-triazine, 1,2,4-triazine, 1,3,5-triazine, 1,2,3-triazole or 1,2,4-triazole.

Physiologically tolerable salts of the compounds of formula I are nontoxic salts that are physiologically acceptable, in particular pharmaceutically utilizable salts. Such salts of compounds of the formula I containing acidic groups, for example a carboxy group COOH, are for example alkali metal salts or alkaline earth metal salts such as sodium salts, potassium salts, magnesium salts and calcium salts, and also salts with physiologically tolerable quaternary ammonium ions such as tetramethylammonium or tetraethylammonium, and acid addition salts with ammonia and physiologically tolerable organic amines, such as methylamine, dimethylamine, trimethylamine, ethylamine, triethylamine, ethanolamine or tris-(2-hydroxyethyl)amine. Basic groups contained in the compounds of the formula I, for example amino groups or amidino groups, form acid addition salts, for example with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. The present invention also includes acid addition salts of compounds of the formula I which contain, for example, two basic groups, with one or two acid equivalents.

Salts of compounds of formula I can be obtained by customary methods known to those skilled in the art, for example by combining a compound of the formula I with an inorganic or organic acid or base in a solvent or diluent, or from other salts by cation exchange or anion exchange. The present invention also includes all salts of the compounds of the formula I which, because of low physiologically tolerability, are not directly suitable for use in pharmaceuticals but are suitable, for example, as intermediates for carrying out further chemical modifications of the compounds of the formula I or as starting materials for the preparation of physiologically tolerable salts.

The anions of the mentioned acids that may be present in acid addition salts of the compounds of the formula I, are also examples of anions that may be present in the compounds of the formula I if they contain one or more positively charged groups like trialkylammonio-substituents, i.e. groups of the formula $(alkyl)_3N^+$ bonded via the positively charged nitrogen atom, representing $R^3$, or quaternized ring nitrogen atoms in heterocyclic groups. In general a compound of the formula I contains one or more physiologically tolerable anions or anion equivalents as counterions if it contains one or more permanently positively charged groups like trialkylammonio.

Optically active carbon atoms present in the compounds of the formula I can independently of each other have R configuration or S configuration. The compounds of the formula I can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formula I, and it comprises all ratios of the stereoisomers in the mixtures. In case the compounds of the formula I can be present as E isomers or Z isomers (or cis isomers or trans isomers) the invention relates both to pure E isomers and pure Z isomers and to E/Z mixtures in all ratios. The invention also comprises all tautomeric forms of the compounds of the formula I.

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formula I can also be obtained by employing stereochemically uniform starting materials or by using stereoselective reactions.

The present invention also relates to processes of preparation by which the compounds of the formula I are obtainable. The compounds of the formula I can generally be prepared by linkage of two or more fragments (or building blocks) which can be derived retrosynthetically from formula I. In the preparation of the compounds of the formula I it can generally be advantageous or necessary in the course of the synthesis to introduce functional groups which could lead to undesired reactions or side reactions in a synthesis step in the form of precursors which are later converted into the desired functional groups. As examples of precursor groups nitro groups may be mentioned which may later be converted into amino groups. Protecting groups (or blocking groups) that may be present on functional groups include allyl, tert-butyl, benzyl, allyloxycarbonyl (Alloc), tert-butoxycarbonyl (Boc), benzyloxycarbonyl (Z) and 9-fluorenylmethoxycarbonyl (Fmoc) as protecting groups for hydroxy, carboxylic acid and amino. In particular, in the preparation of the compounds of the formula I building blocks can be connected by performing one or more condensation reactions and/or substitution reactions such as amide couplings, i.e. by forming an amide bond between a carboxylic acid group of one building block and an amino group of another building block, or by a nucleophilic substitution of a leaving group of one building block by an nucleophilic group of another building block, i.e. by substitution of an halogen of one building block by an amino group of another building block. For example, compounds of the formula I can be prepared by linking the building blocks of the formulae II and III or by linking the building blocks of the formulae IV and V

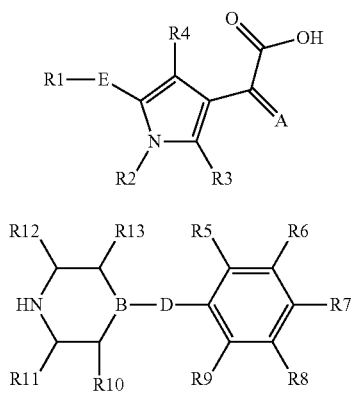

(II)

(III)

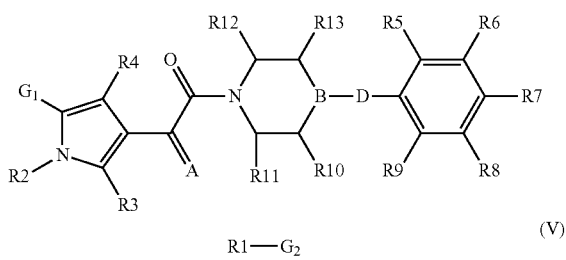

(IV)

(V)

by means of forming in a manner known per se an amide bond or an ester bond between the carboxylic acid group G1 depicted in formula IV and the amino group G2 depicted in formula V or between the carboxylic acid group G1 depicted in formula IV and the hydroxy group G2 depicted in formula V.

The starting compounds of the formulae II, III IV and V and other compounds which are employed in the synthesis of the compounds of formula I for introducing certain structural units, are commercially available or can be readily prepared from commercially available compounds by or analogously to procedures described below or in the literature which is readily available to those skilled in the art, i.e. building block of the formula II can be prepared by a procedure described i.e. in I. K. Khanna et al. J. Med. Chem. 1997, 40, 1619-1633.

Depending upon the substitution pattern, the pyrrole of the formula VII can be

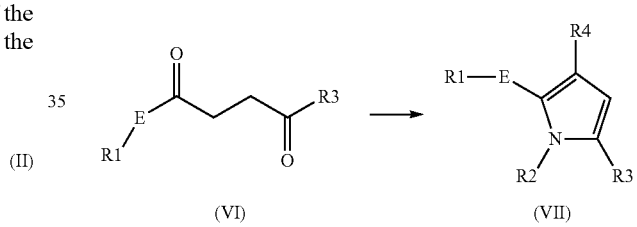

(VI)

(VII)

synthesized from suitable 1,4-diketones of the formula VI. Conversion of the 1,4-diketone building block of the formula VI to the pyrrole of the formula VII can be done by standard Paal-Knorr procedures. For example the cyclisation to the pyrrole of the formula VII can be done by heating of the 1,4-diketone of the formula VI with a suitable amino building block $R_2$—$NH_2$ e.g. ($C_1$-$C_8$)-alkyl-$NH_2$ in an alcohol or by heating building block VI with ammonia, e.g. in the form of an ammonium salt. The reaction can be carried out with ammonium acetate in acetic acid or with ammonium carbonate without a solvent. The 1,4-diketones can be synthesized by using the Stetter reaction conditions (H. Stetter, Angew. Chem. 88 (1976) 695) starting from suitable building blocks of the formulae VIII and IX.

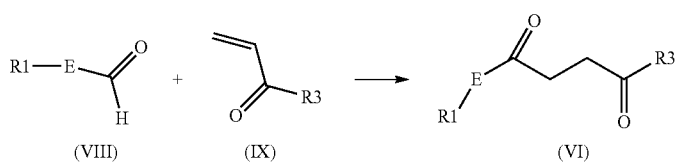

(VIII) (IX) (VI)

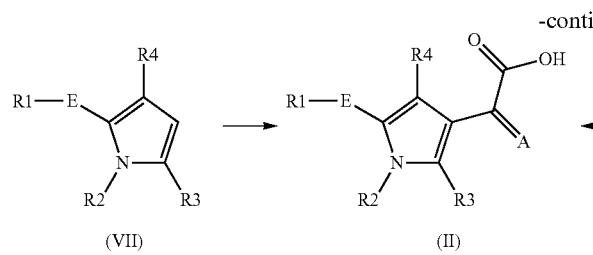

The building block of the formula II can be synthesized by reaction of the building block of the formula VII with oxalyl chloride in THF or alternatively by Friedel-Crafts acylation of the building block of the formula VII with acetyl chloride followed by oxidation of the building block X. For example the oxidation can be done by SeO2 in pyridine or KMnO$_4$/KOH in water or peracetic acid and RuCl$_3$ in ethyl acete/water.

The compounds of the present invention are platelet ADP P2Y12 receptor antagonists, which antagonize the platelet aggregating effect of the activation of the platelet ADP P2Y12 receptors. In particular, they are highly active antagonists of the P2Y12 receptor. They are specific platelet ADP receptor antagonists inasmuch as they do not substantially inhibit or promote the activity of other receptors whose activation or inhibition is not desired. The activity of the compounds of the formula I can be determined, for example, in the assays described below or in other in vitro, ex vivo or in vivo assays known to those skilled in the art. For example, the ability of the compounds to bind to the P2Y12 receptor may be measured by methods similar to those described in prior art and by the assay described below. With respect to P2Y12 binding affinity, a preferred embodiment of the invention comprises compounds which have an IC50<1 mM for P2Y12 binding affinity as determined in the assay described, and which preferably do not substantially influence the activity of other receptors involved in platelet aggregation and fibrinolysis whose inhibition or activation is not desired (using the same concentration of the antagonist). The ability of the compounds to inhibit ADP-induced aggregation of platelets may be measured by methods similar to those described in prior art and by the method described below. The ability of the compounds to inhibit thrombus formation in vivo or ex vivo may be measured by methods similar to those described in prior art. The results of these assays clearly demonstrate that the compounds of the invention are functional antagonists of the platelet adenosine diphosphate receptor and are therefore useful for inhibiting platelet aggregation and thrombus formation.

As platelet ADP P2Y12 receptor antagonists the compounds of the formula I and/or their physiologically tolerable salts and/or their prodrugs are generally suitable for the therapy and prophylaxis of conditions in which the activity of platelet ADP P2Y12 receptor plays a role or has an undesired extent, or which can favorably be influenced by inhibiting P2Y12 receptor or decreasing the activity, or for the prevention, alleviation or cure of which an inhibition of platelet ADP P2Y12 receptor or a decrease in the activity is desired by the physician. As inhibition of the platelet ADP P2Y12 receptor influences platelet activation, platelet aggregation and platelet degranulation and promote platelet disaggregation, the compounds of the formula I and/or their physiologically tolerable salts and/or their prodrugs are generally suitable for reducing blood thrombus formation, or for the therapy and prophylaxis of conditions in which the activity of the platelet aggregation and thus blood coagulation system plays a role or has an undesired extent, or which can favorably be influenced by reducing thrombus formation, or for the prevention, alleviation or cure of which a decreased activity of the platelet aggregation system is desired by the physician. A specific subject of the present invention thus are the reduction or inhibition of unwanted thrombus formation, in particular in an individual, by administering an effective amount of a compound of the formula I and/or a physiologically tolerable salt and/or a prodrug thereof, as well as pharmaceutical preparations thereof.

The present invention also relates to the compounds of the formula I and/or their physiologically tolerable salts and/or their prodrugs for use as pharmaceuticals (or medicaments), to the use of the compounds of the formula I and/or their physiologically tolerable salts and/or their prodrugs for the production of pharmaceuticals for inhibition of the P2Y12 receptor or for influencing platelet activation, platelet aggregation and platelet degranulation and promote platelet disaggregation, inflammatory response or for the therapy or prophylaxis of the diseases mentioned above or below, for example for the production of pharmaceuticals for the therapy and prophylaxis of cardiovascular disorders, thromboembolic diseases or restenosis. The invention also relates to the use of the compounds of the formula I and/or their physiologically tolerable salts and/or their prodrugs for the inhibition of P2Y12 receptor or for influencing platelet activation, platelet aggregation and platelet degranulation and promote platelet disaggregation or for the therapy or prophylaxis of the diseases mentioned above or below, for example for use in the therapy and prophylaxis of cardiovascular disorders, thromboembolic diseases or restenoses, and to methods of treatment aiming at such purposes including methods for said therapies and prophylaxis. The present invention also relates to pharmaceutical preparations (or pharmaceutical compositions) which contain an effective amount of at least one compound of the formula I and/or its physiologically tolerable salts and/or its prodrugs in addition to a customary pharmaceutically acceptable carrier, i.e. one or more pharmaceutically acceptable carrier substances or excipients and/or auxiliary substances or additives.

The invention also relates to the treatment of disease states such as abnormal thrombus formation, acute myocardial infarction, unstable angina, thromboembolism, acute vessel closure associated with thrombolytic therapy or percutaneous transluminal coronary angioplasty (PTCA), transient ischemic attacks, stroke, intermittent claudication or bypass grafting of the coronary or peripheral arteries, vessel luminal narrowing, restenosis post coronary or venous angioplasty, maintenance of vascular access patency in long-term hemodialysis patients, pathologic thrombus formation occurring in the veins of the lower extremities following abdominal, knee or hip surgery, pathologic thrombus formation occurring in the veins of the lower extremities following abdominal, knee and hip surgery, a risk of pulmonary thromboembolism, or disseminated systemic intravascular coagulatopathy occurring in vascular systems during septic shock, certain viral infections or cancer.

The compounds of the present invention can also be used to reduce an inflammatory response. Examples of specific disorders for the treatment or prophylaxis of which the compounds of the formula I can be used are coronary heart disease, myocardial infarction, angina pectoris, vascular restenosis, for example restenosis following angioplasty like PTCA, adult respiratory distress syndrome, multi-organ failure and disseminated intravascular clotting disorder. Examples of related complications associated with surgery are thromboses like deep vein and proximal vein thrombosis, which can occur following surgery.

The compounds of the formula I and their physiologically tolerable salts and their prodrugs can be administered to animals, preferably to mammals, and in particular to humans as pharmaceuticals for therapy or prophylaxis. They can be administered on their own, or in mixtures with one another or in the form of pharmaceutical preparations, which permit enteral or parenteral administration.

The pharmaceuticals can be administered orally, for example in the form of pills, tablets, lacquered tablets, coated tablets, granules, hard and soft gelatine capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carriers being used in addition to the compound(s) of the formula I and/or its (their) physiologically tolerable salts and/or its (their) prodrugs. For the production of pills, tablets, coated tablets and hard gelatine capsules it is possible to use, for example, lactose, cornstarch or derivatives thereof, talc, stearic acid or its salts, etc. Carriers for soft gelatine capsules and suppositories are, for example, fats, waxes, semisolid and liquid polyols, natural or hardened oils, etc. Suitable carriers for the production of solutions, for example injection solutions, or of emulsions or syrups are, for example, water, saline, alcohols, glycerol, polyols, sucrose, invert sugar, glucose, vegetable oils, etc. Suitable carriers for microcapsules, implants or rods are, for example, copolymers of glycolic acid and lactic acid. The pharmaceutical preparations normally contain about 0.5% to 90% by weight of the compounds of the formula I and/or their physiologically tolerable salts and/or their prodrugs. The amount of the active ingredient of the formula I and/or its physiologically tolerable salts and/or its prodrugs in the pharmaceutical preparations normally is from about 0.5 mg to about 1000 mg, preferably from about 1 mg to about 500 mg.

In addition to the active ingredients of the formula I and/or their physiologically acceptable salts and/or prodrugs and to carrier substances, the pharmaceutical preparations can contain additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula I, and/or their physiologically tolerable salts and/or their prodrugs. In case a pharmaceutical preparation contains two or more compounds of the formula I, the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formula I allows a great deal of control over the biological and physico-chemical properties of the compounds and thus allows the selection of such desired compounds. Furthermore, in addition to at least one compound of the formula I and/or a physiologically tolerable salt and/or its prodrug, the pharmaceutical preparations can also contain one or more other therapeutically or prophylactically active ingredients.

In one embodiment of the invention the compound of formula I is administered in combination with a fibrinogen-receptor antagonist, thrombin inhibitor, factor Xa inhibitor, heparins, low-molecular-weight heparins or aspirin. For example, as a fibrinogen-receptor-antagonist can be used the clinically approved GP IIb/IIIa monoclonal antibody abciximab (ReoPro) or eptifibatide (Integrelin) or tirofiban (Aggrastat). Further examples of fibrinogen-receptor antagonists are roxifiban, lotrafiban, orbofiban, sibrafiban and xemilofiban. Examples of thrombin inhibitors are ximelagatran, dabigatran etexilate. As suitable factor Xa inhibitors can be used for example otamixaban, rivaroxaban or apixaban. The compound of formula I can also administered in combination with an indirect faxtor Xa inhibitor like idraparinux or fondaparinux. For example enoxaparin can be used as a low-molecular-weight heparin.

When using the compounds of the formula I the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from 0.01 mg/kg to 100 mg/kg, preferably from 0.1 mg/kg to 50 mg/kg, in particular from 0.1 mg/kg to 10 mg/kg, (in each case in mg per kg of body weight). The daily dose can be divided, in particular in the case of the administration of relatively large amounts, into several, for example 2, 3 or 4, part administrations. As usual, depending on individual behaviour it may be necessary to deviate upwards or downwards from the daily dose indicated.

A compound of the formula I can also advantageously be used as an antiaggregant outside an individual. For example, an effective amount of a compound of the invention can be contacted with a freshly drawn blood sample to prevent aggregation of the blood sample. Further, a compound of the formula I or its salts can be used for diagnostic purposes, for example in in vitro diagnoses, and as an auxiliary in biochemical investigations. For example, a compound of the formula I can be used in an assay to identify the presence of the P2Y12 receptor or to isolate the P2Y12 receptor containing tissue in a substantially purified form. A compound of the invention can be labelled with, for example, a radioisotope, and the labelled compound bound to the P2Y12 receptor is then detected using a routine method useful for detecting the particular label. Thus, a compound of the formula I or a salt thereof can be used as a probe to detect the location or amount of P2Y12 receptors activity in vivo, in vitro or ex vivo.

Furthermore, the compounds of the formula I can be used as synthesis intermediates for the preparation of other compounds, in particular of other pharmaceutical active ingredients, which are obtainable from the compounds of the formula I, for example by introduction of substituents or modification of functional groups.

The general synthetic sequences for preparing the compounds useful in the present invention our outlined in the examples given below. Both an explanation of, and the actual procedure for, the various aspects of the present invention are described where appropriate. The following examples are intended to be merely illustrative of the present invention, and not limiting thereof in either scope or spirit. Those with skill in the art will readily understand that known variations of the conditions and processes described in the examples can be used to synthesize the compounds of the present invention.

It is understood that changes that do not substantially affect the activity of the various embodiments of this invention are included within the invention disclosed herein. Thus, the following examples are intended to illustrate but not limit the present invention.

EXAMPLES

When in the final step of the synthesis of a compound an acid such as trifluoroacetic acid or acetic acid was used, for example when trifluoroacetic acid was employed to an acid-labile protecting group (eg. a tBu group) or when a compound was purified by chromatography using an eluent which contained such an acid, in some cases, depending on the work-up procedure, for example the details of a freeze-drying process, the compound was obtained partially or completely in the form of a salt of the acid used, for example in the form of the acetic acid salt, formic acid salt or trifluoroacetic acid salt or hydrochloric acid salt. Likewise starting materials or intermediates bearing a basic center like for example a basic nitrogen were either obtained and used as free base or in salt form like, for example, a trifluoroacetic acid salt, a hydrobromic acid salt, sulfuric acid salt, or a hydrochloric acid salt.

Abbreviations used:
tert-Butyl tBu
2,2'-bis(diphenylphoshino-1,1'-binaphthyl Binap
Bis-(oxo-3-oxazolidinyl)-phosphoryl chloride BOP—Cl
dibenzylidenacetone dba
Dichloromethane DCM
Dicyclohexyl-carbodiimide DCC
Diethylphosphoryl cyanide DEPC
Diisopropylethyl amine DIPEA
4-Dimethyaminopyridine DMAP
N,N-Dimethylformamide DMF
Dimethylsulfoxide DMSO
1,1'-Bis(diphenylphosphino)ferrocene DPPF
O-(7-Azabenzotriazol-1-yl)-N,N,N',N'-tetramethyluronium-hexafluorophosphate HATU
high performance liquid chromatography HPLC
N-Bromosuccinimide NBS
N-Chlorosuccinimide NCS
N-Iodosuccinimide NIS
N-Ethylmorpholine NEM
Methanol MeOH
Room temperature 20° C. to 25° C. RT
Saturated sat.
Tetrahydrofuran THF
Trifluoroacetic acid TFA
O-((Ethoxycarbonyl)cyanomethyleneamino)-N,N,N',N'-tetramethyluronium tetrafluoroborate TOTU

Example 1

1-(2-Methyl-5-phenyl-1H-pyrrol-3-yl)-2-[4-(3-trifluoromethyl-phenyl)-piperazin-1-yl]-ethane-1,2-dione

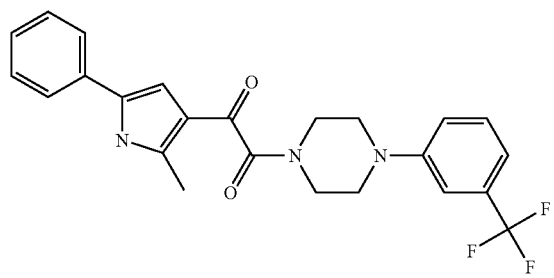

a) 2-Methyl-5-phenyl-1H-pyrrole: To 5.00 g (28.37 mmol) of 1-phenyl-1,4-pentandedione 6.815 g (71 mmol) ammonium carbonate were added. The mixture was heated at 100° C. for 4 days. During this time further 6.815 g ammonium carbonate were added in 1 g portions. The reaction mixture was treated with water and extracted with ethyl acetate. The separated organic layer was dried (MgSO$_4$) and evaporated to yield 4.13 g (93%) of 2-methyl-5-phenyl-1H-pyrrole.

b) (2-Methyl-5-phenyl-1H-pyrrol-3-yl)-oxo-acetic acid: To a stirred solution of 14.32 g (91 mmol) 2-methyl-5-phenyl-1H-pyrrole in 50 ml THF a solution of 11.56 g (91 mmol) oxalyl chloride in 10 ml THF was slowly added at 0° C. The solution was warmed up to RT and stirred for 2 h. The reaction mixture was poured into water, treated with Na$_2$CO$_3$ and extracted with ethyl acetate. The separated organic layer was dried (MgSO$_4$) and evaporated to yield 10.5 g (50%) 2-methyl-5-phenyl-1H-pyrrol-3-yl)-oxo-acetic acid.

c) 1-(2-Methyl-5-phenyl-1H-pyrrol-3-yl)-2-[4-(3-trifluoromethyl-phenyl)-piperazin-1-yl]ethane-1,2-dione: To a solution of 1.00 g (4.362 mmol) of 2-methyl-5-phenyl-1H-pyrrol-3-yl)-oxo-acetic acid in 30 ml of DMF were added 1.431 g (4.362 mmol) TOTU. After 30 min at RT 1.004 g (4.362 mmol) of 1-(3-trifluoromethylphenyl)piperazine and 3.014 g (26.17 mmol) of N-ethylmorpholine were added. After 24 h stirring at RT the solution was evaporated and the residue was treated with a saturated aqueous solution of NaHCO$_3$. The aqueous solution was extracted with ethyl acetate. The separated organic layer was dried (MgSO$_4$) and evaporated. The residue was purified by HPLC and lyophilized to yield 890 mg (37%) of the title compound. MS 442.2 (M+H)$^+$, The following compounds in table 1 were synthesized using the procedures described above:

TABLE 1

| Example | structure | name | MS (ESI+) |
|---|---|---|---|
| 2 | 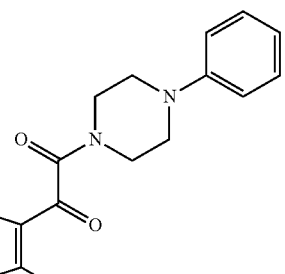 | 1-(2-Methyl-5-phenyl-1H-pyrrol-3-yl)-2-(4-phenyl-piperazin-1-yl)-ethane-1,2-dione | 374.24 |
| 3 | 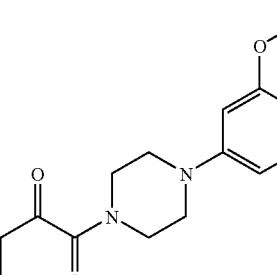 | 1-[4-(3-Methoxy-phenyl)-iperazin-1-yl]-2-(2-methyl-5-phenyl-1H-pyrrol-3-yl)-ethane-1,2-dione | 404.24 |
| 4 | 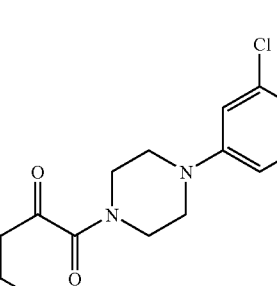 | 1-[4-(3-Chloro-phenyl)-piperazin-1-yl]-2-(2-methyl-5-phenyl-1H-pyrrol-3-yl)-ethane-1,2-dione | 408.19 |
| 5 | 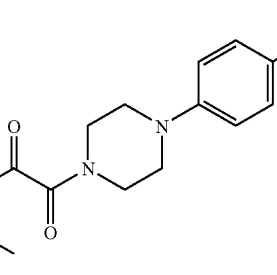 | 1-[4-(4-Chloro-phenyl)-piperazin-1-yl]-2-(2-methyl-5-phenyl-1H-pyrrol-3-yl)-ethane-1,2-dione | 408.19 |
| 6 | 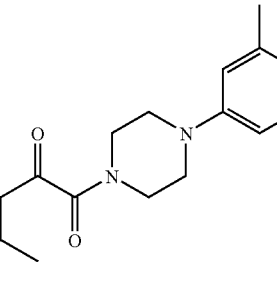 | 1-[4-(3-Methyl-phenyl)-piperazin-1-yl]-2-(2-methyl-5-phenyl-1H-pyrrol-3-yl)-ethane-1,2-dione | 388.22 |

TABLE 1-continued

| Example | structure | name | MS (ESI+) |
|---|---|---|---|
| 7 | 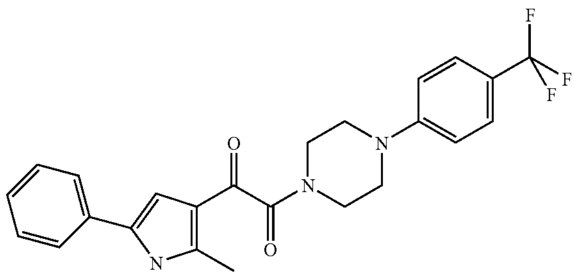 | 1-[4-(4-Trifluoromethyl-phenyl)-piperazin-1-yl]-2-(2-methyl-5-phenyl-1H-pyrrol-3-yl)-ethane-1,2-dione | 442.26 |
| 8 | 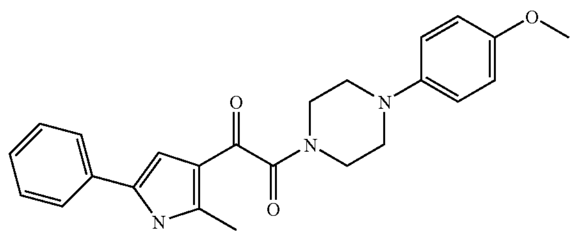 | 1-[4-(4-Methoxy-phenyl)-piperazin-1-yl]-2-(2-methyl-5-phenyl-1H-pyrrol-3-yl)-ethane-1,2-dione | 388.22 |
| 9 | 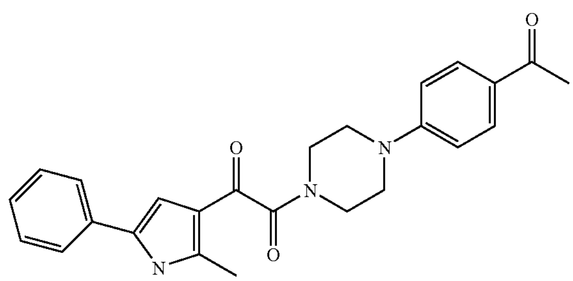 | 1-[4-(4-Acetyl-phenyl)-piperazin-1-yl]-2-(2-methyl-5-phenyl-1H-pyrrol-3-yl)-ethane-1,2-dione | 408.19 |
| 10 | 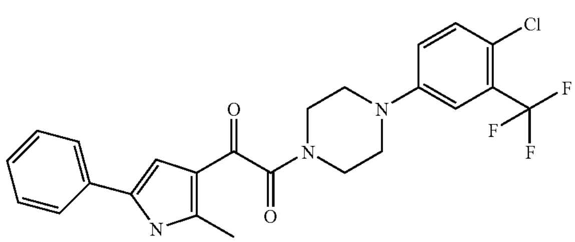 | 1-[4-(4-Chloro-3-trifluoromethyl-phenyl)-piperazin-1-yl]-2-(2-methyl-5-phenyl-1H-pyrrol-3-yl)-ethane-1,2-dione | 476.26 |
| 11 | 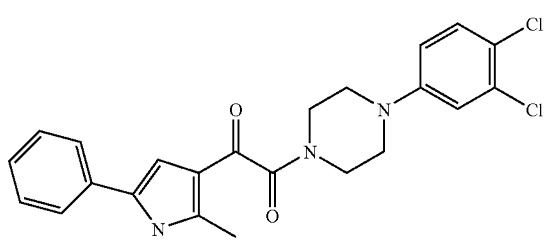 | 1-[4-(3,4-Dichloro-phenyl)-piperazin-1-yl]-2-(2-methyl-5-phenyl-1H-pyrrol-3-yl)-ethane-1,2-dione | 442.19 |
| 12 | 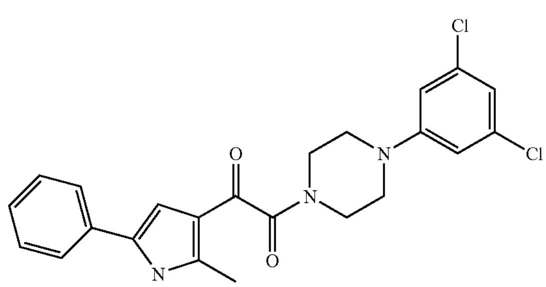 | 1-[4-(3,5-Dichloro-phenyl)-piperazin-1-yl]-2-(2-methyl-5-phenyl-1H-pyrrol-3-yl)-ethane-1,2-dione | 442.19 |

TABLE 1-continued

| Example | structure | name | MS (ESI+) |
|---|---|---|---|
| 13 | 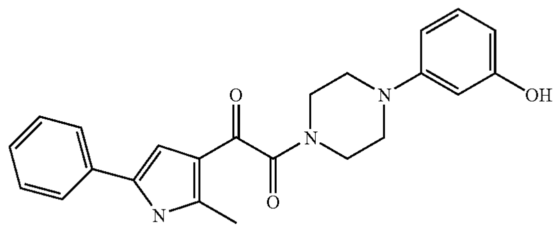 | 1-[4-(3-Hydroxy-phenyl)-piperazin-1-yl]-2-(2-methyl-5-phenyl-1H-pyrrol-3-yl)-ethane-1,2-dione | 390.16 |
| 14 | 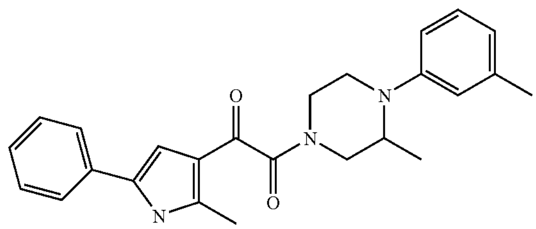 | 1-(2-Methyl-5-phenyl-1H-pyrrol-3-yl)-2-(3-methyl-4-m-tolyl-piperazin-1-yl)-ethane-1,2-dione | 402.19 |
| 15 | 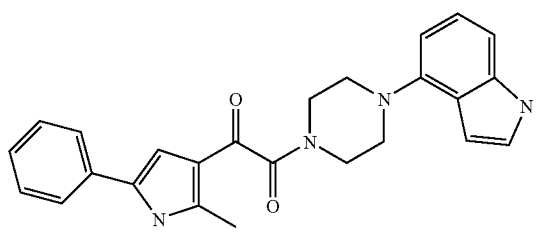 | 1-[4-(1H-Indol-4-yl)-piperazin-1-yl]-2-(2-methyl-5-phenyl-1H-pyrrol-3-yl)-ethane-1,2-dione | 413.19 |
| 16 | 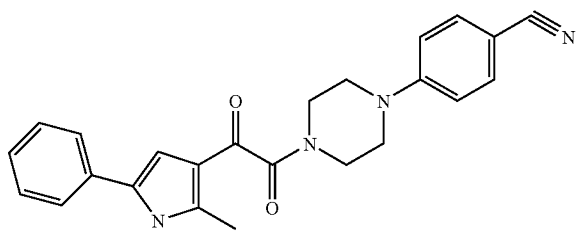 | 4-{4-[2-(2-Methyl-5-phenyl-1H-pyrrol-3-yl)-2-oxo-acetyl]-piperazin-1-yl}-benzonitrile | 399.18 |
| 17 | 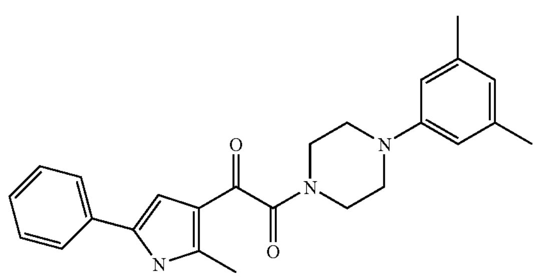 | 1-[4-(3,5-Dimethyl-phenyl)-piperazin-1-yl]-2-(2-methyl-5-phenyl-1H-pyrrol-3-yl)-ethane-1,2-dione | 402.18 |
| 18 | 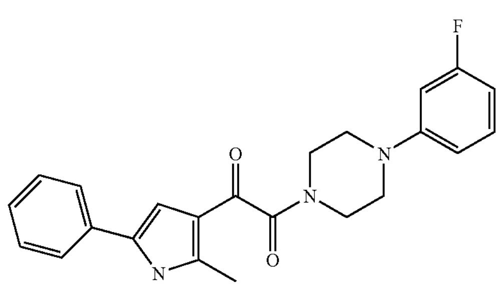 | 1-[4-(3-Fluoro-phenyl)-piperazin-1-yl]-2-(2-methyl-5-phenyl-1H-pyrrol-3-yl)-ethane-1,2-dione | 392.16 |

TABLE 1-continued

| Example | structure | name | MS (ESI+) |
|---|---|---|---|
| 19 | 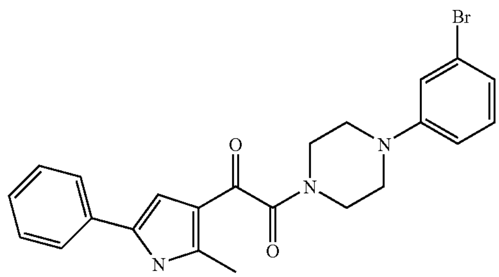 | 1-[4-(3-Bromo-phenyl)-piperazin-1-yl]-2-(2-methyl-5-phenyl-1H-pyrrol-3-yl)-ethane-1,2-dione | 454.08 |
| 20 | 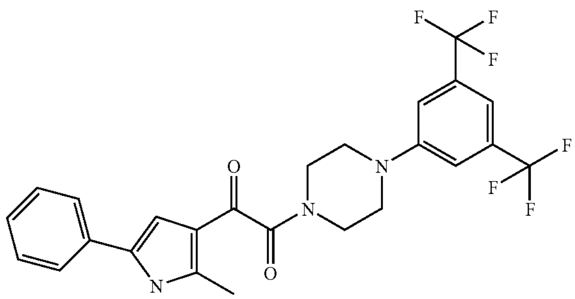 | 1-[4-(3,5-Bis-trifluoromethyl-phenyl)-piperazin-1-yl]-2-(2-methyl-5-phenyl-1H-pyrrol-3-yl)-ethane-1,2-dione | 510.15 |
| 21 | 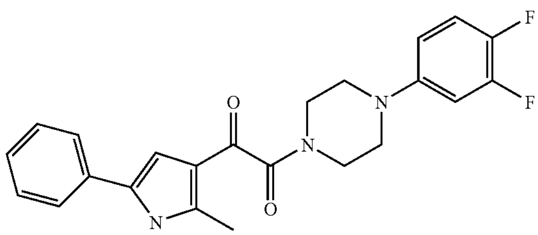 | 1-[4-(3,4-Difluoro-phenyl)-piperazin-1-yl]-2-(2-methyl-5-phenyl-1H-pyrrol-3-yl)-ethane-1,2-dione | 410.15 |
| 22 | 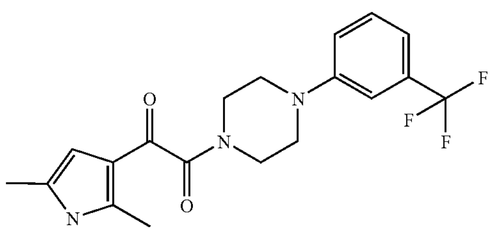 | 1-(2,5-Dimethyl-1H-pyrrol-3-yl)-2-[4-(3-trifluoromethyl-phenyl)-piperazin-1-yl]-ethane-1,2-dione | 380.18 |
| 23 | 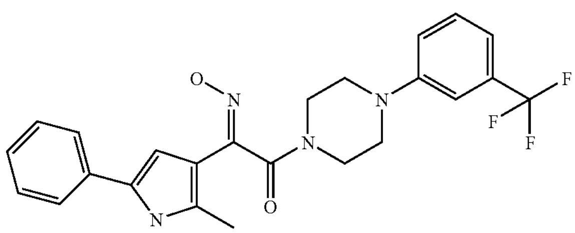 | 1-(2-Methyl-5-phenyl-1H-pyrrol-3-yl)-2-[4-(3-trifluoromethyl-phenyl)-piperazin-1-yl]-ethane-1,2-dione 1-oxime | 457.19 |
| 24 | 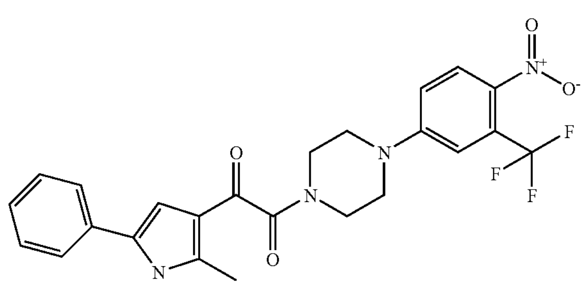 | 1-(2-Methyl-5-phenyl-1H-pyrrol-3-yl)-2-[4-(4-nitro-3-trifluoromethyl-phenyl)-piperazin-1-yl]-ethane-1,2-dione | 487.34 |

TABLE 1-continued

| Example | name | MS (ESI+) |
|---|---|---|
| 25 | 1-[4-(3-Chloro-4-fluoro-phenyl)-piperazin-1-yl]-2-(2-methyl-5-phenyl-1H-pyrrol-3-yl)-ethane-1,2-dione | 426.29 |
| 26 | 1-[4-(2,3-Dihydro-benzo[1,4]dioxin-6-yl)-piperazin-1-yl]-2-(2-methyl-5-phenyl-1H-pyrrol-3-yl)-ethane-1,2-dione | 432.35 |
| 27 | 3-(3-{2-Oxo-2-[4-(3-trifluoromethyl-phenyl)-piperazin-1-yl]-acetyl}-5-phenyl-1H-pyrrol-2-yl)-propionic acid | 500.47 |
| 28 | 2-(3-{4-[2-(2-Methyl-5-phenyl-1H-pyrrol-3-yl)-2-oxo-acetyl]-piperazin-1-yl}-phenoxy)-acetamide | 447.50 |
| 29 | (3-{4-[2-(2-Methyl-5-phenyl-1H-pyrrol-3-yl)-2-oxo-acetyl]-piperazin-1-yl}-phenoxy)-acetic acid ethyl ester | 476.52 |
| 30 | 1-(2-Methyl-5-phenyl-1H-pyrrol-3-yl)-2-{4-[3-(2-iperidin-1-yl-ethoxy)--phenyl]-iperazin-1-yl}-ethane-1,2-dione | 501.32 |

TABLE 1-continued

| Example | structure | name | MS (ESI+) |
|---|---|---|---|
| 31 | 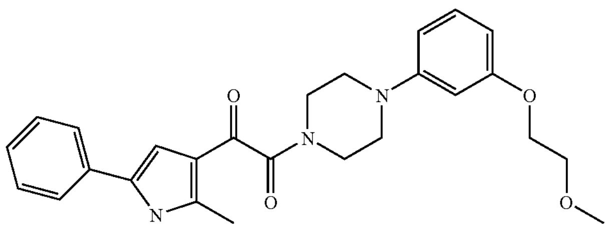 | 1-{4-[3-(2-Methoxy-ethoxy)-phenyl]-piperazin-1-yl}-2-(2-methyl-5-phenyl-1H-pyrrol-3-yl)-ethane-1,2-dione | 448.23 |
| 32 | 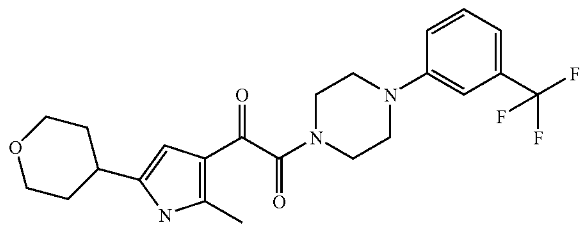 | 1-[2-Methyl-5-(tetrahydro-pyran-4-yl)-1H-pyrrol-3-yl]-2-[4-(3-trifluoromethyl-phenyl)-piperazin-1-yl]-ethane-1,2-dione | 450.33 |
| 33 | 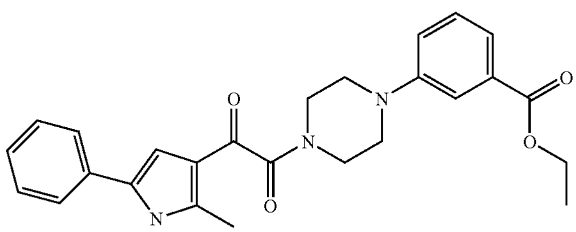 | 3-{4-[2-(2-Methyl-5-phenyl-1H-pyrrol-3-yl)-2-oxo-acetyl]-piperazin-1-yl}-benzoic acid ethyl ester | 446.25 |
| 34 | 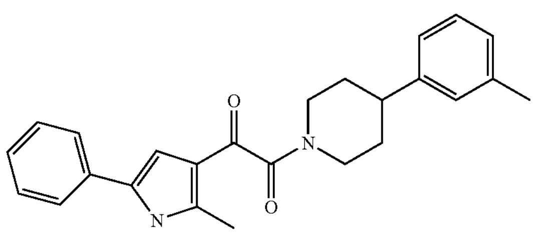 | 1-(2-Methyl-5-phenyl-1H-pyrrol-3-yl)-2-(4-m-tolyl-piperidin-1-yl)-ethane-1,2-dione | 387.20 |
| 35 | 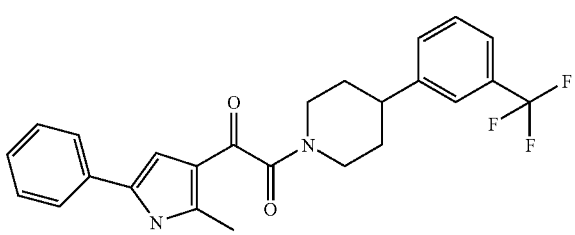 | 1-(2-Methyl-5-phenyl-1H-pyrrol-3-yl)-2-[4-(3-trifluoromethyl-phenyl)-piperidin-1-yl]-ethane-1,2-dione | 441.17 |
| 36 | 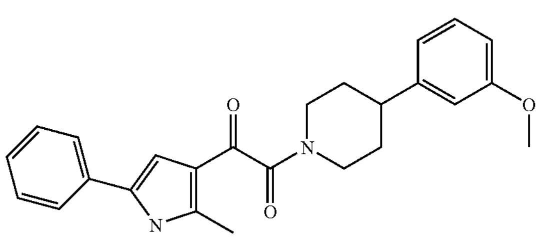 | 1-(2-Methyl-5-phenyl-1H-pyrrol-3-yl)-2-[4-(3-methoxy-phenyl)-piperidin-1-yl]-ethane-1,2-dione | 403.20 |

TABLE 1-continued

| Example | structure | name | MS (ESI+) |
|---|---|---|---|
| 37 | 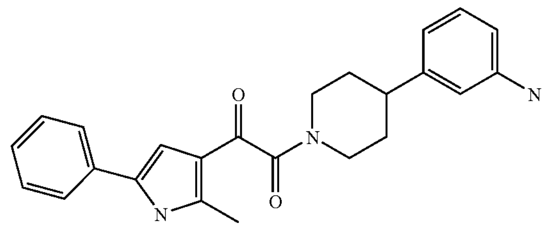 | 1-[4-(3-Amino-phenyl)-piperidin-1-yl]-2-(2-methyl-5-phenyl-1H-pyrrol-3-yl)-ethane-1,2-dione | 388.19 |
| 38 | 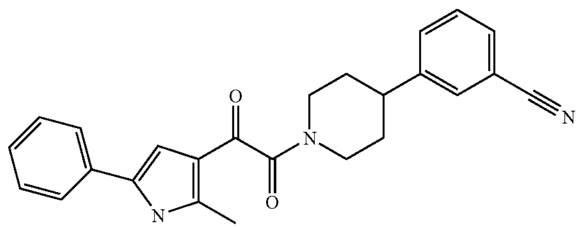 | 3-{1-[2-(2-Methyl-5-phenyl-1H-pyrrol-3-yl)-2-oxo-acetyl]-piperidin-4-yl}-benzonitrile | 398.18 |
| 39 | 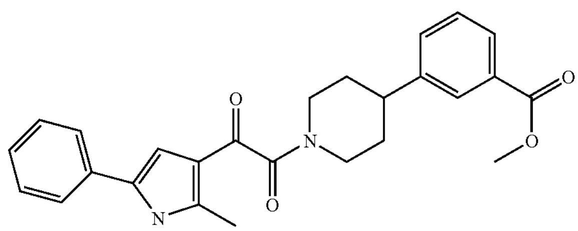 | 3-{1-[2-(2-Methyl-5-phenyl-1H-pyrrol-3-yl)-2-oxo-acetyl]-piperidin-4-yl}-benzoic acid methyl ester | 431.18 |
| 40 | 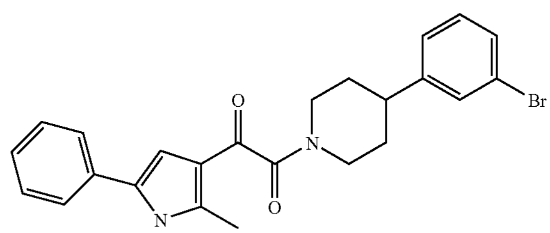 | 1-[4-(3-Bromo-phenyl)-piperidin-1-yl]-2-(2-methyl-5-phenyl-1H-pyrrol-3-yl)-ethane-1,2-dione | 451.14 |
| 41 | 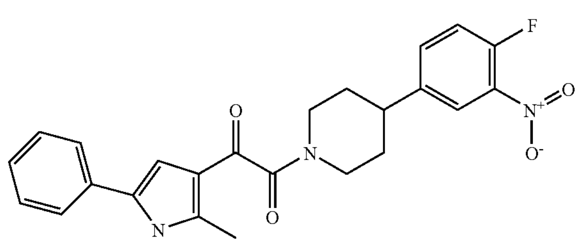 | 1-[4-(4-Fluoro-3-nitro-phenyl)-piperidin-1-yl]-2-(2-methyl-5-phenyl-1H-pyrrol-3-yl)-ethane-1,2-dione | 436.33 |
| 42 | 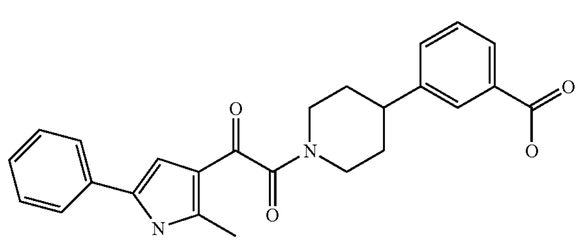 | 3-{1-[2-(2-Methyl-5-phenyl-1H-pyrrol-3-yl)-2-oxo-acetyl]-piperidin-4-yl}-benzoic acid | 417.29 |

TABLE 1-continued

| Example | structure | name | MS (ESI+) |
|---|---|---|---|
| 43 | 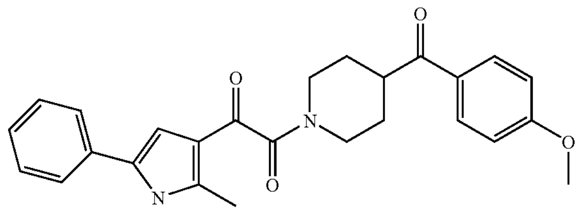 | 1-[4-(4-Methoxy-benzoyl)-piperidin-1-yl]-2-(2-methyl-5-phenyl-1H-pyrrol-3-yl)-ethane-1,2-dione | 431.26 |
| 44 | 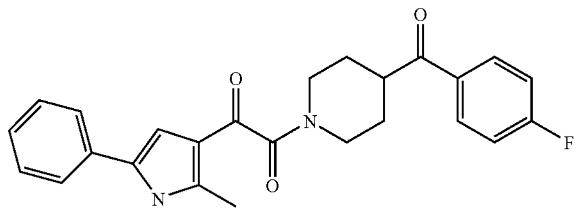 | 1-[4-(4-Fluoro-benzoyl)-piperidin-1-yl]-2-(2-methyl-5-phenyl-1H-pyrrol-3-yl)-ethane-1,2-dione | 419.24 |
| 45 | 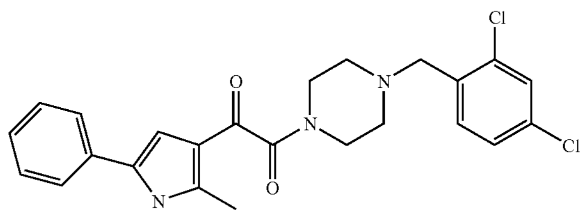 | 1-[4-(2,4-Dichloro-benzyl)-piperazin-1-yl]-2-(2-methyl-5-phenyl-1H-pyrrol-3-yl)-ethane-1,2-dione | 456.20 |
| 46 | 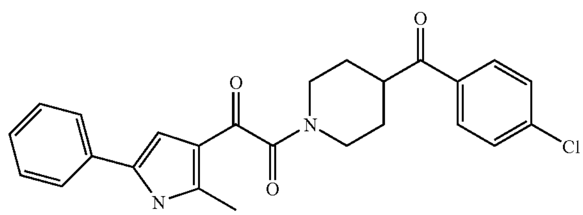 | 1-[4-(4-Chloro-benzoyl)-piperidin-1-yl]-2-(2-methyl-5-phenyl-1H-pyrrol-3-yl)-ethane-1,2-dione | 435.23 |
| 47 | 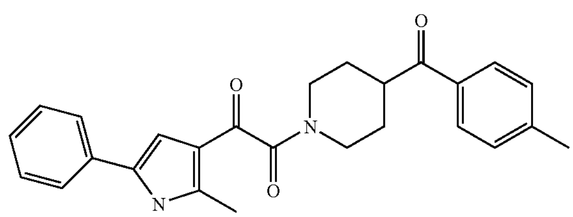 | 1-[4-(4-Methyl-benzoyl)-piperidin-1-yl]-2-(2-methyl-5-phenyl-1H-pyrrol-3-yl)-ethane-1,2-dione | 415.34 |
| 48 | 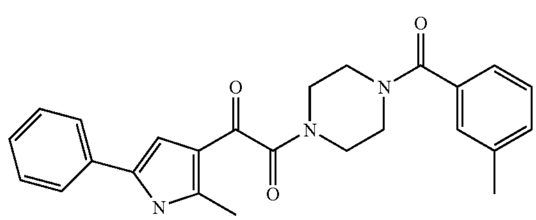 | 1-[4-(3-Methyl-benzoyl)-piperazin-1-yl]-2-(2-methyl-5-phenyl-1H-pyrrol-3-yl)-ethane-1,2-dione | 416.34 |
| 49 | 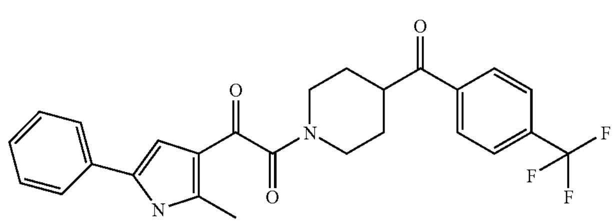 | 1-(2-Methyl-5-phenyl-1H-pyrrol-3-yl)-2-[4-(4-trifluoromethyl-benzoyl)-piperidin-1-yl]-ethane-1,2-dione | 469.22 |

TABLE 1-continued

| Example | structure | name | MS (ESI+) |
|---|---|---|---|
| 50 | 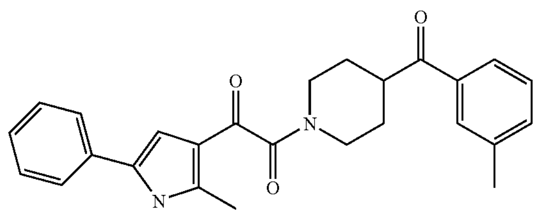 | 1-[4-(3-Methyl-benzoyl)-piperidin-1-yl]-2-(2-methyl-5-phenyl-1H-pyrrol-3-yl)-ethane-1,2-dione | 415.23 |
| 51 | 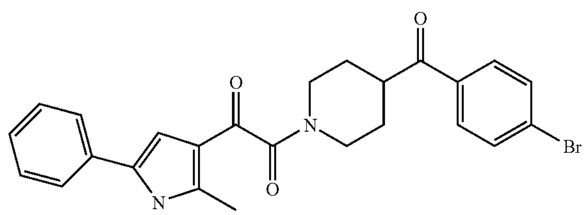 | 1-[4-(4-Bromo-benzoyl)-piperidin-1-yl]-2-(2-methyl-5-phenyl-1H-pyrrol-3-yl)-ethane-1,2-dione | 481.16 |
| 52 | 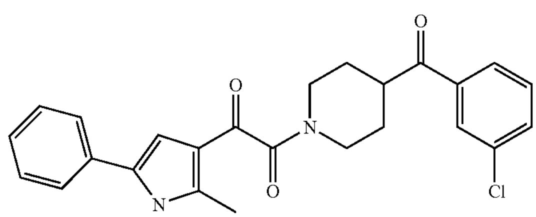 | 1-[4-(3-Chloro-benzoyl)-piperidin-1-yl]-2-(2-methyl-5-phenyl-1H-pyrrol-3-yl)-ethane-1,2-dione | 435.21 |
| 53 | 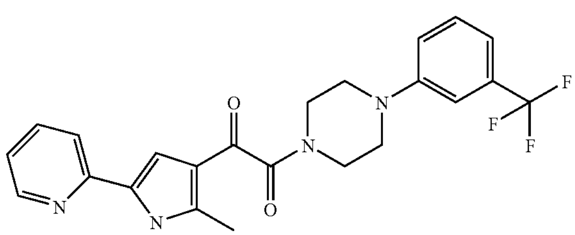 | 1-(2-Methyl-5-pyridin-2-yl-1H-pyrrol-3-yl)-2-[4-(3-trifluoromethyl-phenyl)-piperazin-1-yl]-ethane-1,2-dione | 443.17 |
| 54 | 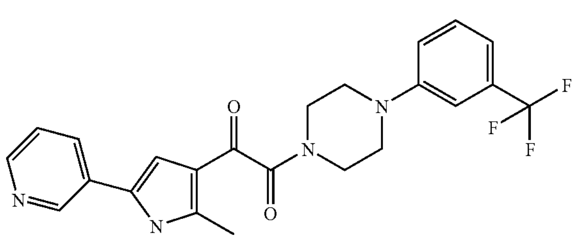 | 1-(2-Methyl-5-pyridin-3-yl-1H-pyrrol-3-yl)-2-[4-(3-trifluoromethyl-phenyl)-piperazin-1-yl]-ethane-1,2-dione | 443.17 |

Example 55

3,5-Dimethyl-4-{2-oxo-2-[4-(3-trifluoromethyl-phenyl)-piperazin-1-yl]-acetyl}-1H-pyrrole-2-carboxylic acid ethyl ester

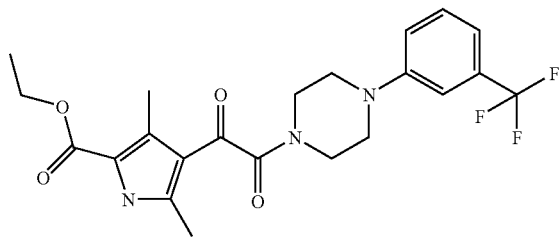

a) 3,5-Dimethyl-4-oxalyl-1H-pyrrole-2-carboxylic acid ethyl ester: To a solution of 0.2 g (0.956 mmol) 4-acetyl-3,5-dimethyl-1H-pyrrole-2-carboxylic acid ethyl ester in 3 ml pyridine 0.318 g (2.868 mmol) $SeO_2$ were added under argon. The reaction mixture was stirred at 100° C. for 4 h. The mixture was filtered off and 20 ml of a NaOH (5%) were added to the solution. The aqueous phase was extracted with diethylether and then the aqueous phase was acidified with 1 N HCl. The aqueous solution was extracted with ethyl acetate. Then the organic phase was washed with brine and dried over anhydrous magnesium sulfate. The solvent was evaporated to yield 180 mg (79%) of the title compound.

b) 3,5-Dimethyl-4-{2-oxo-2-[4-(3-trifluoromethyl-phenyl)-piperazin-1-yl]-acetyl}-1H-pyrrole-2-carboxylic acid ethyl ester: To a solution of 0.15 g (0.627 mmol) of 3,5-dimethyl-4-oxalyl-1H-pyrrole-2-carboxylic acid ethyl ester in 3 ml of DMF were added 0.205 g (0.627 mmol) TOTU. After 30 min at RT 0.144 g (0.627 mmol) of 1-(3-trifluoromethylphenyl)piperazine and 0.216 g (1.881 mmol) of N-ethylmorpholine were added. After 24 h stirring at RT the solution was evaporated and the residue was treated with a saturated aqueous solution of $NaHCO_3$. The aqueous solution was extracted with ethyl acetate. The separated organic layer was dried ($MgSO_4$) and evaporated. The residue was purified by HPLC and lyophilized to yield 120 mg (28%) of the title compound. MS 452.17 $(M+H)^+$,

Example 56

3,5-Dimethyl-4-{2-oxo-2-[4-(3-trifluoromethyl-phenyl)-piperazin-1-yl]-acetyl}-1H-pyrrole-2-carboxylic acid

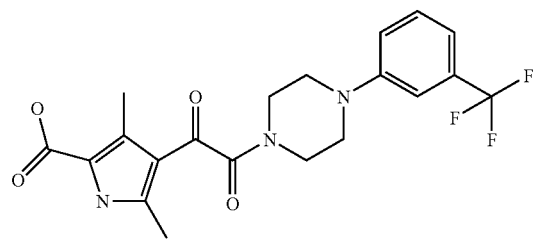

To a solution of 0.100 g (0.221 mmol) 3,5-dimethyl-4-{2-oxo-2-[4-(3-trifluoromethyl-phenyl)-piperazin-1-yl]-acetyl}-1H-pyrrole-2-carboxylic acid ethyl ester in 2 ml ethanol and 1 ml water 0.018 g (0.443 mmol) NaOH were added. The solution was stirred at 80° C. for 5 h. The solvent was evaporated and 1 N HCl was added to the residue. The precipitate was filtered off and dried to yield 80 mg (85%) of the title compound. MS 424.15 $(M+H)^+$, The following compounds in table 2 were synthesized starting from example 56 using the TOTU procedure described above:

TABLE 2

| Example | structure | name | MS (ESI+) |
|---|---|---|---|
| 57 | 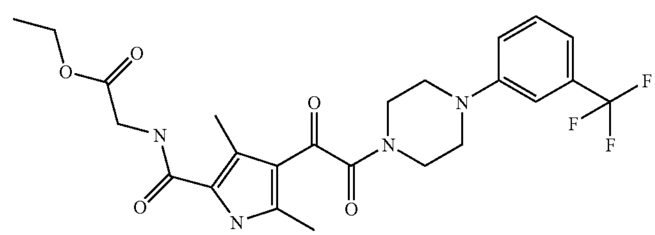 | [(3,5-Dimethyl-4-{2-oxo-2-[4-(3-trifluoromethyl-phenyl)-iperazin-1-yl]-acetyl}-1H-pyrrole-2-carbonyl)-amino]-acetic acid ethyl ester | 509.32 |
| 58 | 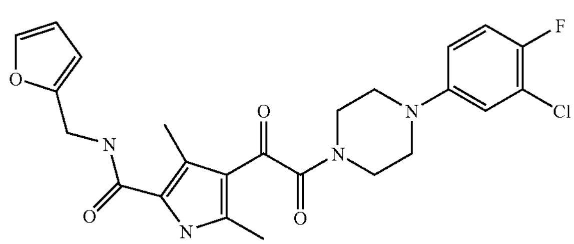 | 4-{2-[4-(3-Chloro-4-fluoro-phenyl)-piperazin-1-yl]-2-oxo-acetyl}-3,5-dimethyl-1H-pyrrole-2-carboxylic acid (furan-2-ylmethyl)-amide | 487.22 |

TABLE 2-continued

| Example | name | MS (ESI+) |
|---|---|---|
| 59 | 4-{2-[4-(4-Chloro-3-trifluoromethyl-phenyl)-piperazin-1-yl]-2-oxo-acetyl}-3,5-dimethyl-1H-pyrrole-2-carboxylic acid (furan-2-ylmethyl)-amide | 537.21 |
| 60 | 4-{2-[4-(4-Chloro-3-trifluoromethyl-phenyl)-piperazin-1-yl]-2-oxo-acetyl}-3,5-dimethyl-1H-pyrrole-2-carboxylic acid cyclopropylmethyl-amide | 511.23 |
| 61 | 4-{2-[4-(4-Chloro-3-trifluoromethyl-phenyl)-piperazin-1-yl]-2-oxo-acetyl}-3,5-dimethyl-1H-pyrrole-2-carboxylic acid propylamide | 499.22 |
| 62 | 4-{2-[4-(3-Chloro-4-fluoro-phenyl)-piperazin-1-yl]-2-oxo-acetyl}-3,5-dimethyl-1H-pyrrole-2-carboxylic acid cyclopropylmethyl-amide | 461.20 |
| 63 | 4-{2-[4-(3-Chloro-phenyl)-piperazin-1-yl]-2-oxo-acetyl}-3,5-dimethyl-1H-pyrrole-2-carboxylic acid cyclopropylamide | 429.23 |

TABLE 2-continued

| Example | name | MS (ESI+) |
|---|---|---|
| 64 | 4-{2-[4-(4-Chloro-3-trifluoromethyl-phenyl)-piperazin-1-yl]-2-oxo-acetyl}-3,5-dimethyl-1H-pyrrole-2-carboxylic acid (pyridin-3-ylmethyl)-amide | 548.22 |
| 65 | 3,5-Dimethyl-4-{2-oxo-2-[4-(3-trifluoromethyl-phenyl)-piperazin-1-yl]-acetyl}-1H-pyrrole-2-carboxylic acid propylamide | 465.27 |
| 66 | 3,5-Dimethyl-4-{2-oxo-2-[4-(3-trifluoromethyl-phenyl)-piperazin-1-yl]-acetyl}-1H-pyrrole-2-carboxylic acid (furan-2-ylmethyl)-amide | 503.26 |
| 67 | 4-{2-[4-(3-Chloro-phenyl)-piperazin-1-yl]-2-oxo-acetyl}-3,5-dimethyl-1H-pyrrole-2-carboxylic acid (furan-2-ylmethyl)-amide | 469.24 |
| 68 | 4-{2-[4-(3-Chloro-phenyl)-piperazin-1-yl]-2-oxo-acetyl}-3,5-dimethyl-1H-pyrrole-2-carboxylic acid cyclopropylmethyl-amide | 443.25 |

Example 69

1-(4-Bromo-2-methyl-5-phenyl-1H-pyrrol-3-yl)-2-[4-(3-trifluoromethyl-phenyl)-piperazin-1-yl]ethane-1,2-dione

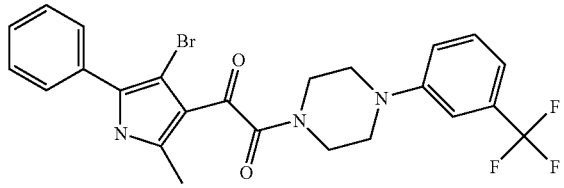

To a solution of 970 mg (2.197 mmol) 1-(2-Methyl-5-phenyl-1H-pyrrol-3-yl)-2-[4-(3-trifluoromethyl-phenyl)-piperazin-1-yl]ethane-1,2-dione in 10 ml acetonitrile 981 mg (4.394 mmol) Cu(II)Br$_2$ were added. After stirring the mixture for 4 h at RT the solvent was removed and the residue was treated with ethyl acetate and aqueous NH$_3$ solution at 0° C. The separated organic layer was dried (MgSO$_4$) and evaporated to give 840 mg (73%) of the title compound. MS 519.08 (M+H)$^+$.

Example 70

(E)-3-(5-Methyl-4-{2-oxo-2-[4-(3-trifluoromethyl-phenyl)-piperazin-1-yl]-acetyl}-2-phenyl-1H-pyrrol-3-yl)-acrylic acid methyl ester

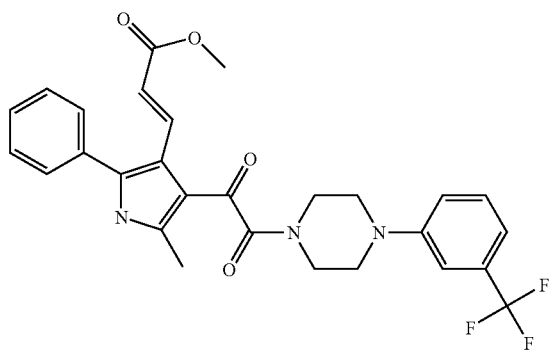

To a solution of 200 mg (0.384 mmol) 1-(4-bromo-2-methyl-5-phenyl-1H-pyrrol-3-yl)-2-[4-(3-trifluoromethyl-phenyl)-piperazin-1-yl]ethane-1,2-dione in 4 ml DMF 453 mg (5.266 mmol) methyl acrylate and 1.5 ml triethylamine were added. The solution was degassed and backfilled with argon whereupon 38 mg (0.053 mmol) bis(triphenylphosphine(palladium(II)-chloride were added. The mixture was heated at 110° C. for 4 h. The solvent was evaporated and the residue was treated with water and extracted with ethyl acetate. The organic layer was dried (MgSO$_4$) and evaporated. The residue was purified by HPLC and lyophilized to yield 88 mg (44%) of the title compound. MS 526.20 (M+H)$^+$.

Example 71

(E)-3-(5-Methyl-4-{2-oxo-2-[4-(3-trifluoromethyl-phenyl)-piperazin-1-yl]-acetyl}-2-phenyl-1H-pyrrol-3-yl)-acrylic acid

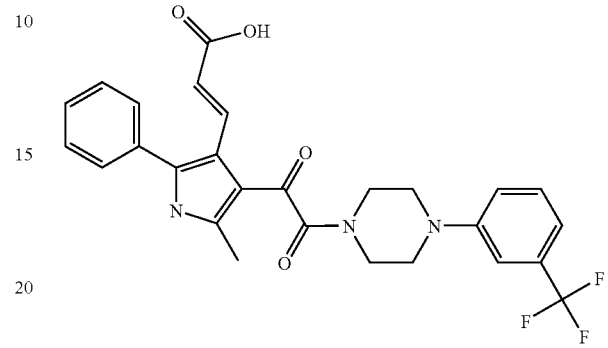

To a solution of 155 mg (0.295 mmol) (E)-3-(5-methyl-4-{2-oxo-2-[4-(3-trifluoromethyl-phenyl)-piperazin-1-yl]-acetyl}-2-phenyl-1H-pyrrol-3-yl)-acrylic acid methyl ester in 2 ml ethanol 12 mg ((0.295 mmol) sodium hydroxide and 0.5 ml water were added. The mixture was stirred for 24 h at RT. The solvent was evaporated and the residue was treated with 1N HCl. The precipitate was filtered off and dried to give 120 mg (80%) of the title compound. MS 512.17 (M+H)$^+$.

Pharmacological Testing

Human P2Y12 Recombinant Cell Membrane Binding Assay

The ability of a test compound to bind to the P2Y12 receptor was evaluated in a recombinant cell membrane binding assay. In this competitive binding assay, the test compound competed against a radiolabeled agonist for binding to the P2Y12 receptor, expressed on the cell membrane. Inhibition of binding of the labeled material was measured and correlated to the amount and potency of the test compound. This binding assay is a modification of the procedure described by Takasaki, J. et. al, Mol. Pharmacol., 2001, Vol. 60, pg. 432.

As source of P2Y12, a membrane preparation was prepared from Chinese Hamster Ovary (CHO) cells with recombinant expression of the human P2Y12 receptor according to standard procedures.

To a 96-well microtiterplate the following were added: a) 24 µl of assay buffer (10 mM HEPES, 138 mM NaCl, 2.9 mN KCl, 12 mM NaHCO$_3$, 1 mM EDTA-Na, 0.1% BSA, pH 7.4) b) 1 µL compound in DMSO c) 50 µL P2Y12 CHO membrane (20 µg/ml) and after 15 min at RT d) 25 µL of 1.61 nM $^{33}$P 2MeS—ADP (Perkin Elmer NEN custom synthesis, specific activity ~2100 Ci/mmol) made in assay buffer.

After 20 min incubation at RT samples were transferred to 96-well microtiter filterplates (Millipore HTS GF/B), pre-wetted for 20 min with 300 µL of stop buffer (10 mM HEPES, 138 mM NaCl pH 7.4) and then filtered through completely with a Millipore plate vacuum. Next, wells were washed four times with 400 µl/well of stop buffer on a plate vacuum. The plate was disassembled and allowed to air dry overnight with the filter side up over night. The filter plates were snapped into adapter plates and 0.1 mL of Microscint 20 Scintillation Fluid (Perkin Elmer #6013621) was added to each well. The top of the filterplate was sealed with plastic plate covers. The sealed filterplate were incubated 2 hours at room temperature. A Microbeta Scintillation Counter was used to measure counts. The binding of compound is expressed as a % inhibition of specific binding, defined by subtraction of the background with 1 mM ADP. Compounds were diluted as 10 mM DMSO stocks and tested in a four-point, five-fold dilution series run in triplicate beginning at 10 µM, final concentration. Data were analyzed using a four-parameter curve fit with a fixed minimum and maximum experimentally defined as the average positive and negative controls on each plate.

The results (inhibition MeSADP binding P2Y12, IC50 in mikro M (µM) are shown in Table 3:

TABLE 3

| Example | IC 50 [µM] |
|---------|------------|
| 1       | 0.5        |
| 10      | 0.7        |
| 33      | 0.17       |
| 51      | 0.71       |
| 52      | 0.52       |
| 71      | 0.03       |

Inhibition of Human Platelet Aggregation

Alternatively to a binding assay which measures a compound's ability to bind to the P2Y12 receptor, the effect on cellular function can also be determined. This ability of the compound can be evaluated in two platelet aggregation assays: in 96-well plates and with the "Born"-method using single cuvettes.

96-Well Assay:

Whole blood was collected from healthy volunteers using 20 ml syringes containing 2 ml of ACD-A Aqua-Citrat-Dextrose-A, Fresenius). The anticoagulated whole blood was transferred into 15 ml polypropylene conical tubes (10 ml per tube). The tubes were centrifuged for 15 minutes at 150×g at room temperature without using the centrifuge brake. This procedure leads to a pellet of cellular components and a supernatant of platelet rich plasma (PRP). The PRP layer was collected from each tube and pooled for each donor. To avoid carry over of cellular components following centrifugation, approximately 5 ml of PRP was left in the tube. The platelet concentration was determined using a Coulter Counter.

The 15 ml tubes containing the pellet of cellular components were centrifuged again for 10 minutes at 1940×g. This pelleted out most particulate blood constituents remaining, leaving a layer of Platelet Poor Plasma (PPP). The PPP was collected for each donor. The PRP layer, previously set aside, was diluted with PPP to a final concentration of approximately 3×E8 platelets/ml with the PPP.

The human platelet aggregation assay is performed in 96-well plates using a microtiter plate reader (SpectraMax Plus 384 with SoftMax Pro software from Molecular Devices). In the plate 15 µl of test compound at 10× final concentration in NaCl is mixed with 120 µl fresh PRP and incubated for 5 minutes. Following that incubation period, 15 µl of 40 µM ADP is added to the reaction mix. This addition of ADP is sufficient to induce aggregation in the absence of an inhibitor. The plates are then transferred to the microplate reader and aggregation is measured over 20 minutes. The instrument settings include: Absorbance at 650 nm, run time 20 minutes with readings in 1-minute intervals and 50 seconds shaking between readings all performed at 37° C. Results of the assay are expressed as % inhibition, and are calculated using area under curve (AUC) of the absorbance over 20 minutes.

"Born"-Method:

Whole blood was collected from healthy volunteers using 20 ml syringes containing 2 ml of buffered Citrate. The anticoagulated whole blood was transferred into 15 ml polypropylene conical tubes (10 ml per tube). The tubes were centrifuged for 15 minutes at 340×g at room temperature without using the centrifuge brake. This procedure leads to a pellet of cellular components and a supernatant of platelet rich plasma (PRP). The PRP layer was collected from each tube and pooled for each donor. To avoid carry over of cellular components following centrifugation, approximately 5 ml of PRP was left in the tube. The platelet concentration was determined using a Coulter Counter.

The 15 ml tubes containing the pellet of cellular components were centrifuged again for 10 minutes at 1940×g. This pelleted out most particulate blood constituents remaining, leaving a layer of Platelet Poor Plasma (PPP). The PPP was collected for each donor. The PRP layer, previously set aside, was diluted with PPP to a final concentration of approximately 3×E8 platelets/ml with the PPP.

The human platelet aggregation assay is performed in single use cuvettes using the platelet aggregation profiler (PAP-4 or -8, Bio/Data corporation).

In the assay cuvette 4 µl of test compound at 100× final concentration in DMSO is mixed with 392 µl fresh PRP and incubated for 2 minutes at 37° C. with 1.200 rpm stirring. Following that incubation period, 4 µl of 250 µM ADP is added to the reaction mix. This addition of ADP is sufficient to induce aggregation in the absence of an inhibitor. After that aggregation is measured over 6 minutes at 37° C. with 1.200 rpm stirring. Results of the assay are expressed as % inhibition, and are calculated using maximum aggregation (Tmax) or area under curve (AUC) of the absorbance over 6 minutes.

What is claimed is:
1. A compound of formula I,

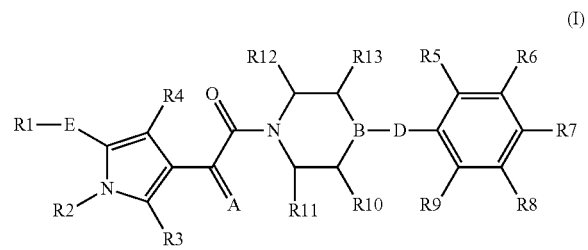

(I)

wherein
R1 is
1) hydrogen atom,
2) —($C_1$-$C_8$)-alkyl,
3) —($C_0$-$C_4$)-alkylene-($C_3$-$C_8$)-cycloalkyl, wherein cycloalkyl is unsubstituted or mono-, di- or trisubstituted independently of one another by halogen,
4) —($C_0$-$C_4$)-alkylene-($C_6$-$C_{14}$)-aryl, and wherein aryl is unsubstituted or mono-, di- or trisubstituted independently of one another by R15, or
5) —($C_0$-$C_4$)-alkylene-heterocyclyl, wherein heterocyclyl is mono or bicyclic and contains 3 to 15 ring carbon atoms and wherein one or more of the ring carbon atoms are replaced by 1, 2, 3 or 4 heteroatoms chosen from nitrogen, sulfur or oxygen,
and wherein said heterocyclyl is unsubstituted or mono-, di- or trisubstituted independently of one another by R14;

E is
1) a covalent bond,
2) —NH—C(O)— or
3) —O—C(O)—,
R2 is
1) hydrogen atom or
2) —($C_1$-$C_8$)-alkyl,
R3 is
1) —($C_1$-$C_8$)-alkyl,
2) —$CF_3$, or
3) —($C_1$-$C_8$)-alkylene-C(O)—O—R16,
R4 is
1) hydrogen atom,
2) —($C_1$-$C_8$)-alkyl,
3) —($C_1$-$C_8$)-alkylene-C(O)—O—R16,
4) —($C_2$-$C_6$)-alkenylene-C(O)—O—R16,
5) —($C_3$-$C_8$)-cycloalkyl-C(O)—O—R16, or
6) halogen,
A is selected from oxygen atom or N—OH,
B is selected from nitrogen atom or CH,
D is
1) a covalent bond,
2) —C(O)— or
3) —$CH_2$—,
R5, R6, R7, R8 and R9 are independently of one another selected from
1) hydrogen atom,
2) —($C_1$-$C_8$)-alkyl, wherein alkyl is unsubstituted or mono-, di- or trisubstituted independently of one another by halogen,
3) —($C_0$-$C_4$)-alkylene-O—R16,
4) halogen,
5) —($C_0$-$C_4$)-alkylene-O—($C_1$-$C_8$)-alkylene-O—R16,
6) —$NO_2$,
7) —CN,
8) —($C_0$-$C_4$)-alkylene-N(R16)-R17,
9) —($C_0$-$C_4$)-alkylene-C(O)—R16,
10) —($C_0$-$C_4$)-alkylene-C(O)—O—R16,
11) —($C_0$-$C_4$)-alkylene-C(O)—N(R16)-R17,
12) —O—($C_0$-$C_4$)-alkylene-C(O)—O—R16,
13) —O—($C_0$-$C_4$)-alkylene-C(O)—N(R16)-R17
14) —($C_0$-$C_4$)-alkylene-($C_3$-$C_{15}$)-heterocyclyl, wherein heterocyclyl is un-substituted or mono-, di- or trisubstituted independently of one another by R14, or
15) —O—($C_0$-$C_4$)-alkylene-($C_3$-$C_{15}$)-heterocyclyl, wherein heterocyclyl is un-substituted or mono-, di- or trisubstituted independently of one another by R14, or
R5 and R6 or R6 and R7 form together with the atoms which they are attached to a 5-, 6- or 7-membered carbon ring, wherein said carbon ring is aromatic, partially unsaturated or saturated, or in which one, two or three of the 5 to 7 ring carbon atoms are replaced by heteroatoms such as nitrogen, oxygen or sulfur, and wherein said carbon ring is unsubstituted or substituted one, two, three or four times by R15, R10, R11, R12 and R13 are independently of one another selected from
1) hydrogen atom,
2) —($C_1$-$C_8$)-alkyl,
3) =O or
4) —OH,
R14 is halogen, —OH, =O, —($C_1$-$C_8$)-alkyl, —O—($C_1$-$C_8$)-alkyl, —$CF_3$, —O—$CF_3$, —$NO_2$, —CN or —$NH_2$,
R15 is halogen, —OH, —($C_1$-$C_8$)-alkyl, —O—($C_1$-$C_8$)-alkyl, —$CF_3$, —O—$CF_3$, —$NO_2$, —CN, —C(O)OH, —C(O)O—($C_1$-$C_8$)-alkyl, —C(O)$NH_2$ or —$NH_2$,
R16 is hydrogen atom, —($C_1$-$C_8$)-alkyl or —($C_0$-$C_4$)-alkylene-($C_3$-$C_8$)-cycloalkyl,
R17 is hydrogen atom or —($C_1$-$C_8$)-alkyl, or
R17 and R16 form together with the nitrogen atom to which they are attached a 5-, 6- or 7-membered carbon ring, wherein said carbon ring is unsaturated or saturated, or in which one, two or three of the 5 to 7 ring carbon atoms are replaced by heteroatoms such as nitrogen, oxygen or sulfur, and wherein said carbon ring is unsubstituted or substituted one, two, three or four times by R15,
in all its stereoisomeric forms and mixtures thereof in any ratio, and its physiologically tolerable salts.

2. A compound as claimed in claim 1, wherein
R1 is
1) —($C_1$-$C_8$)-alkyl,
2) —($C_0$-$C_4$)-alkylene-($C_3$-$C_8$)-cycloalkyl, wherein cycloalkyl is selected from cyclopropyl, cyclobutyl, cyclopentyl, cyclohexyl, cyloheptyl or cyclooctyl and is unsubstituted or mono-, di- or trisubstituted independently of one another by halogen,
3) —($C_0$-$C_4$)-alkylene-($C_6$-$C_{14}$)-aryl, and wherein aryl is selected from phenyl, naphthyl, biphenylyl, indanyl, anthryl or fluorenyl and is unsubstituted or mono-, di- or trisubstituted independently of one another by R15, or
4) —($C_0$-$C_4$)-alkylene-heterocyclyl, wherein heterocyclyl is selected from acridinyl, 8-aza-bicyclo[3.2.1]oct-3-yl, azaindole (1H-pyrrolopyridinyl), azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, and is unsubstituted or mono-, di- or trisubstituted independently of one another by R14;

E is
1) a covalent bond,
2) —NH—C(O)— or
3) —O—C(O)—,

R2 is
1) hydrogen atom or
2) —($C_1$-$C_8$)-alkyl,

R3 is
1) —($C_1$-$C_8$)-alkyl, or
2) —($C_1$-$C_8$)-alkylene-C(O)—O—R16,

R4 is
1) hydrogen atom,
2) —($C_2$-$C_6$)-alkenylene-C(O)—O—R16,
3) —($C_1$-$C_8$)-alkyl or
4) halogen, A is selected from oxygen atom or N—OH,
B is selected from nitrogen atom or CH,
D is
1) a covalent bond,
2) —C(O)— or
3) —$CH_2$—, R5, R6, R7, R8 and R9 are independently of one another selected from
1) hydrogen atom,
2) —($C_1$-$C_8$)-alkyl,
3) —($C_0$-$C_4$)-alkylene-O—R16,
4) halogen,
5) —($C_0$-$C_4$)-alkylene-O—($C_1$-$C_8$)-alkylene-O—R16,
6) —$NO_2$,
7) —CN,
8) —($C_0$-$C_4$)-alkylene-N(R16)-R17,
9) —($C_0$-$C_4$)-alkylene-C(O)—R16,
10) —($C_0$-$C_4$)-alkylene-C(O)—O—R16,
11) —($C_0$-$C_4$)-alkylene-C(O)—N(R16)-R17,
12) —O—($C_0$-$C_4$)-alkylene-C(O)—O—R16,
13) —O—($C_0$-$C_4$)-alkylene-C(O)—N(R16)-R17
14) —($C_0$-$C_4$)-alkylene-($C_3$-$C_{15}$)-heterocyclyl, wherein heterocyclyl is as defined above and is un-substituted or mono-, di- or trisubstituted independently of one another by R14, or
15) —O—($C_0$-$C_4$)-alkylene-($C_3$-$C_{15}$)-heterocyclyl, wherein heterocyclyl is as defined above and is un-substituted or mono-, di- or trisubstituted independently of one another by R14, or R5 and R6 or R6 and R7 form together with the atoms which they are attached to a 5-, 6- or 7-membered carbon ring selected from cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, cycloheptenyl, cyclohepta-1,3-dienyl, cyclohepta-1,4-dienyl, cyclohepta-1,3,5-trienyl, phenyl, 1,4 diazepane, 1,2-diazepine, 1,3-diazepine, 1,4-diazepine, diaziridine, diazirine, dihydroimidazolone, dioxazole, dioxazine, 1,4-dioxine, dioxole, 1,3-dioxolene, 1,3-dioxolane, furan, imidazole, imidazoline, imidazolidine, imidazolidinone, isothiazole, isothiazolidine, isothiazoline, isoxazole, isoxazoline, isoxazolidine, morpholine, 1,2-oxathiepane, 1,2-oxathiolane, 1,4-oxazepane, 1,2-oxazine, 1,3-oxazine, 1,4-oxazine, oxazolone, oxazole, [1,3,4] oxathiazinane 3,3-dioxide, oxaziridine, oxazolidinone, oxetan, oxirane, piperazine, piperidine, pyran, pyrazine, pyrazole, pyrazoline, pyrazolidine, pyridazine, pyridine, pyridinone, pyrimidine, pyrimidine-2,4-dione, pyrrole, pyrrolidine, pyrrolidinone, pyrroline, tetrahydrofuran, tetrahydropyran, tetrahydropyridine, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiomorpholine 1,1-dioxide thiopyran, 1,2,3-triazine, 1,2,4-triazine, 1,3,5-triazine, 1,2,3-triazole or 1,2,4-triazole, and wherein said carbon ring is unsubstituted or substituted one, two, three or four times by R15, R10, R11, R12 and R13 are independently of one another selected from
1) hydrogen atom,
2) —($C_1$-$C_8$)-alkyl or
3) —OH, R14 is halogen, —OH, =O, —($C_1$-$C_8$)-alkyl, —O—($C_1$-$C_8$)-alkyl, —$CF_3$, —O—$CF_3$, —$NO_2$, —CN or —$NH_2$, R15 is halogen, —OH, —($C_1$-$C_8$)-alkyl, —O—($C_1$-$C_8$)-alkyl, —$CF_3$, —O—$CF_3$, —$NO_2$, —CN or —$NH_2$, R16 is hydrogen atom or —($C_1$-$C_8$)-alkyl,
R17 is hydrogen atom or —($C_1$-$C_8$)-alkyl,
in all their stereoisomeric forms and mixtures thereof in any ratio, and their physiologically tolerable salts.

3. A compound as claimed in claim 1, wherein

R1 is
1) —($C_1$-$C_4$)-alkyl,
2) —($C_0$-$C_2$)-alkylene-($C_3$-$C_6$)-cycloalkyl, wherein cycloalkyl is selected from cyclopropyl, cyclobutyl, cyclopentyl or cyclohexyl,
3) —($C_0$-$C_2$)-alkylene-phenyl, or
4) —($C_0$-$C_2$)-alkylene-heterocyclyl, wherein heterocyclyl is selected from furanyl, pyridyl or tetrahydropyranyl, E is
1) a covalent bond,
2) —NH—C(O)— or
3) —O—C(O)—, R2 is hydrogen atom,
R3 is
1) —($C_1$-$C_4$)-alkyl, or
2) —($C_1$-$C_4$)-alkylene-C(O)—O—R16, R4 is
1) hydrogen atom,
2) -ethenylene-C(O)—O—R16, or
3) —($C_1$-$C_4$)-alkyl, A is selected from oxygen atom or N—OH,
B is selected from nitrogen atom or CH,
D is
1) a covalent bond,
2) —C(O)— or
3) —$CH_2$—, R5, R6, R7, R8 and R9 are independently of one another selected from
1) hydrogen atom,
2) —($C_1$-$C_4$)-alkyl,
3) —O—R16,
4) chlorine,
5) fluorine,
6) —O—($C_1$-$C_4$)-alkylene-O—R16,
7) —$NO_2$,
8) —CN,
9) —$NH_2$,
10) —C(O)—R16,
11) —C(O)—O—R16,
12) —($C_0$-$C_4$)-alkylene-C(O)—N(R16)-R17,
13) —O—($C_1$-$C_4$)-alkylene-C(O)—O—R16,
14) —O—($C_1$-$C_4$)-alkylene-C(O)—N(R16)-R17, or
15) —O—($C_1$-$C_4$)-alkylene-piperidinyl, or R5 and R6 or R6 and R7 form together with the atoms which they are attached to a ring selected from 1,4-dioxine or pyrrole,
R10, R11, R12 and R13 are independently of one another selected from
1) hydrogen atom or
2) —($C_1$-$C_4$)-alkyl,
R16 is hydrogen atom or —($C_1$-$C_4$)-alkyl, and
R17 is hydrogen atom or —($C_1$-$C_4$)-alkyl,
in all their stereoisomeric forms and mixtures thereof in any ratio, and their physiologically tolerable salts.

4. A compound as claimed in claim 1, wherein
R1 is -phenyl,
E is a covalent bond,
R2 is hydrogen atom,
R3 is
1) —($C_1$-$C_4$)-alkyl, or
2) —($C_1$-$C_4$)-alkylene-C(O)—O—R16,
R4 is
1) hydrogen atom or
2) -ethenylene-C(O)—O—R16,
3) —($C_1$-$C_4$)-alkyl,
A is oxygen atom,
B is nitrogen atom,
D is a covalent bond,
R5, R6, R7, R8 and R9 are independently of one another selected from
1) hydrogen atom,
2) —($C_1$-$C_4$)-alkyl,
3) —O—R16,
4) chlorine,
5) fluorine,
6) —O—($C_1$-$C_4$)-alkylene-O—R16,
7) —$NO_2$,
8) —CN,
9) —$NH_2$,
10) —C(O)—R16,
11) —C(O)—O—R16,
12) —($C_0$-$C_4$)-alkylene-C(O)—N(R16)-R17,
13) —O—($C_1$-$C_4$)-alkylene-C(O)—O—R16,
14) —O—($C_1$-$C_4$)-alkylene-C(O)—N(R16)-R17 or
15) —O—($C_1$-$C_4$)-alkylene-piperidinyl, or
R5 and R6 or R6 and R7 form together with the atoms which they are attached to a ring selected from 1,4-dioxine or pyrrole,
R10, R11, R12 and R13 are each a hydrogen atom,
R16 is hydrogen atom or —($C_1$-$C_4$)-alkyl, and
R17 is hydrogen atom or —($C_1$-$C_4$)-alkyl,
in all their stereoisomeric forms and mixtures thereof in any ratio, and their physiologically tolerable salts.

5. A compound as claimed in claim 1, wherein the compound is
1-(2-Methyl-5-phenyl-1H-pyrrol-3-yl)-2-[4-(3-trifluoromethyl-phenyl)-piperazin-1-yl]-ethane-1,2-dione,
1-(2-Methyl-5-phenyl-1H-pyrrol-3-yl)-2-(4-phenyl-piperazin-1-yl)-ethane-1,2-dione,
1-[4-(3-Methoxy-phenyl)-piperazin-1-yl]-2-(2-methyl-5-phenyl-1H-pyrrol-3-yl)-ethane-1,2-dione,
1-[4-(3-Chloro-phenyl)-piperazin-1-yl]-2-(2-methyl-5-phenyl-1H-pyrrol-3-yl)-ethane-1,2-dione,
1-[4-(4-Chloro-phenyl)-piperazin-1-yl]-2-(2-methyl-5-phenyl-1H-pyrrol-3-yl)-ethane-1,2-dione,
1-[4-(3-Methyl-phenyl)-piperazin-1-yl]-2-(2-methyl-5-phenyl-1H-pyrrol-3-yl)-ethane-1,2-dione,
1-[4-(4-Trifluoromethyl-phenyl)-piperazin-1-yl]-2-(2-methyl-5-phenyl-1H-pyrrol-3-yl)-ethane-1,2-dione,
1-[4-(4-Methoxy-phenyl)-piperazin-1-yl]-2-(2-methyl-5-phenyl-1H-pyrrol-3-yl)-ethane-1,2-dione,
1-[4-(4-Acetyl-phenyl)-piperazin-1-yl]-2-(2-methyl-5-phenyl-1H-pyrrol-3-yl)-ethane-1,2-dione,
1-[4-(4-Chloro-3-trifluoromethyl-phenyl)-piperazin-1-yl]-2-(2-methyl-5-phenyl-1H-pyrrol-3-yl)-ethane-1,2-dione,
1-[4-(3,4-Dichloro-phenyl)-piperazin-1-yl]-2-(2-methyl-5-phenyl-1H-pyrrol-3-yl)-ethane-1,2-dione,
1-[4-(3,5-Dichloro-phenyl)-piperazin-1-yl]-2-(2-methyl-5-phenyl-1H-pyrrol-3-yl)-ethane-1,2-dione,
1-[4-(3-Hydroxy-phenyl)-piperazin-1-yl]-2-(2-methyl-5-phenyl-1H-pyrrol-3-yl)-ethane-1,2-dione,
1-(2-Methyl-5-phenyl-1H-pyrrol-3-yl)-2-(3-methyl-4-m-tolyl-piperazin-1-yl)-ethane-1,2-dione,
1-[4-(1H-Indol-4-yl)-piperazin-1-yl]-2-(2-methyl-5-phenyl-1H-pyrrol-3-yl)-ethane-1,2-dione,
4-{4-[2-(2-Methyl-5-phenyl-1H-pyrrol-3-yl)-2-oxo-acetyl]-piperazin-1-yl}-benzonitrile,
1-[4-(3,5-Dimethyl-phenyl)-piperazin-1-yl]-2-(2-methyl-5-phenyl-1H-pyrrol-3-yl)-ethane-1,2-dione,
1-[4-(3-Fluoro-phenyl)-piperazin-1-yl]-2-(2-methyl-5-phenyl-1H-pyrrol-3-yl)-ethane-1,2-dione,
1-[4-(3-Bromo-phenyl)-piperazin-1-yl]-2-(2-methyl-5-phenyl-1H-pyrrol-3-yl)-ethane-1,2-dione,
1-[4-(3,5-Bis-trifluoromethyl-phenyl)-piperazin-1-yl]-2-(2-methyl-5-phenyl-1H-pyrrol-3-yl)-ethane-1,2-dione,
1-[4-(3,4-Difluoro-phenyl)-piperazin-1-yl]-2-(2-methyl-5-phenyl-1H-pyrrol-3-yl)-ethane-1,2-dione,
1-(2,5-Dimethyl-1H-pyrrol-3-yl)-2-[4-(3-trifluoromethyl-phenyl)-piperazin-1-yl]-ethane-1,2-dione,
1-(2-Methyl-5-phenyl-1H-pyrrol-3-yl)-2-[4-(3-trifluoromethyl-phenyl)-piperazin-1-yl]-ethane-1,2-dione 1-oxime,
1-(2-Methyl-5-phenyl-1H-pyrrol-3-yl)-2-[4-(4-nitro-3-trifluoromethyl-phenyl)-piperazin-1-yl]-ethane-1,2-dione,
1-[4-(3-Chloro-4-fluoro-phenyl)-piperazin-1-yl]-2-(2-methyl-5-phenyl-1H-pyrrol-3-yl)-ethane-1,2-dione,
1-[4-(2,3-Dihydro-benzo[1,4]dioxin-6-yl)-piperazin-1-yl]-2-(2-methyl-5-phenyl-1H-pyrrol-3-yl)-ethane-1,2-dione,
3-(3-{2-oxo-2-[4-(3-trifluoromethyl-phenyl)-piperazin-1-yl]-acetyl}-5-phenyl-1H-pyrrol-2-yl)-propionic acid,
2-(3-{4-[2-(2-Methyl-5-phenyl-1H-pyrrol-3-yl)-2-oxo-acetyl]-piperazin-1-yl}-phenoxy)-acetamide,
(3-{4-[2-(2-Methyl-5-phenyl-1H-pyrrol-3-yl)-2-oxo-acetyl]-piperazin-1-yl}-phenoxy)-acetic acid ethyl ester,
1-(2-Methyl-5-phenyl-1H-pyrrol-3-yl)-2-{4-[3-(2-piperidin-1-yl-ethoxy)-phenyl]-piperazin-1-yl}-ethane-1,2-dione,
1-{4-[3-(2-Methoxy-ethoxy)-phenyl]-piperazin-1-yl}-2-(2-methyl-5-phenyl-1H-pyrrol-3-yl)-ethane-1,2-dione,
1-[2-Methyl-5-(tetrahydro-pyran-4-yl)-1H-pyrrol-3-yl]-2-[4-(3-trifluoromethyl-phenyl)-piperazin-1-yl]-ethane-1,2-dione,
3-{4-[2-(2-Methyl-5-phenyl-1H-pyrrol-3-yl)-2-oxo-acetyl]-piperazin-1-yl}-benzoic acid ethyl ester,
1-(2-Methyl-5-phenyl-1H-pyrrol-3-yl)-2-(4-m-tolyl-piperidin-1-yl)-ethane-1,2-dione,
1-(2-Methyl-5-phenyl-1H-pyrrol-3-yl)-2-[4-(3-trifluoromethyl-phenyl)-piperidin-1-yl]-ethane-1,2-dione,
1-(2-Methyl-5-phenyl-1H-pyrrol-3-yl)-2-[4-(3-methoxy-phenyl)-piperidin-1-yl]-ethane-1,2-dione,
1-[4-(3-Amino-phenyl)-piperidin-1-yl]-2-(2-methyl-5-phenyl-1H-pyrrol-3-yl)-ethane-1,2-dione, 3-{1-[2-(2-Methyl-5-phenyl-1H-pyrrol-3-yl)-2-oxo-acetyl]-piperidin-4-yl}-benzonitrile,
3-{1-[2-(2-Methyl-5-phenyl-1H-pyrrol-3-yl)-2-oxo-acetyl]-piperidin-4-yl}-benzoic acid methyl ester,
1-[4-(3-Bromo-phenyl)-piperidin-1-yl]-2-(2-methyl-5-phenyl-1H-pyrrol-3-yl)-ethane-1,2-dione,
1-[4-(4-Fluoro-3-nitro-phenyl)-piperidin-1-yl]-2-(2-methyl-5-phenyl-1H-pyrrol-3-yl)-ethane-1,2-dione,
3-{1-[2-(2-Methyl-5-phenyl-1H-pyrrol-3-yl)-2-oxo-acetyl]-piperidin-4-yl}-benzoic acid,
1-[4-(4-Methoxy-benzoyl)-piperidin-1-yl]-2-(2-methyl-5-phenyl-1H-pyrrol-3-yl)-ethane-1,2-dione,
1-[4-(4-Fluoro-benzoyl)-piperidin-1-yl]-2-(2-methyl-5-phenyl-1H-pyrrol-3-yl)-ethane-1,2-dione,
1-[4-(2,4-Dichloro-benzyl)-piperazin-1-yl]-2-(2-methyl-5-phenyl-1H-pyrrol-3-yl)-ethane-1,2-dione,
1-[4-(4-Chloro-benzoyl)-piperidin-1-yl]-2-(2-methyl-5-phenyl-1H-pyrrol-3-yl)-ethane-1,2-dione,
1-[4-(4-Methyl-benzoyl)-piperidin-1-yl]-2-(2-methyl-5-phenyl-1H-pyrrol-3-yl)-ethane-1,2-dione,
1-[4-(3-Methyl-benzoyl)-piperazin-1-yl]-2-(2-methyl-5-phenyl-1H-pyrrol-3-yl)-ethane-1,2-dione,
1-(2-Methyl-5-phenyl-1H-pyrrol-3-yl)-2-[4-(4-trifluoromethyl-benzoyl)-piperidin-1-yl]-ethane-1,2-dione,
1-[4-(3-Methyl-benzoyl)-piperidin-1-yl]-2-(2-methyl-5-phenyl-1H-pyrrol-3-yl)-ethane-1,2-dione,
1-[4-(4-Bromo-benzoyl)-piperidin-1-yl]-2-(2-methyl-5-phenyl-1H-pyrrol-3-yl)-ethane-1,2-dione,
1-[4-(3-Chloro-benzoyl)-piperidin-1-yl]-2-(2-methyl-5-phenyl-1H-pyrrol-3-yl)-ethane-1,2-dione,
1-(2-Methyl-5-pyridin-2-yl-1H-pyrrol-3-yl)-2-[4-(3-trifluoromethyl-phenyl)-piperazin-1-yl]-ethane-1,2-dione,
1-(2-Methyl-5-pyridin-3-yl-1H-pyrrol-3-yl)-2-[4-(3-trifluoromethyl-phenyl)-piperazin-1-yl]-ethane-1,2-dione,
3,5-Dimethyl-4-{2-oxo-2-[4-(3-trifluoromethyl-phenyl)-piperazin-1-yl]-acetyl}-1H-pyrrole-2-carboxylic acid ethyl ester,
3,5-Dimethyl-4-{2-oxo-2-[4-(3-trifluoromethyl-phenyl)-piperazin-1-yl]-acetyl}-1H-pyrrole-2-carboxylic acid,
[(3,5-Dimethyl-4-{2-oxo-2-[4-(3-trifluoromethyl-phenyl)-piperazin-1-yl]-acetyl}-1H-pyrrole-2-carbonyl)-amino]-acetic acid ethyl ester,
4-{2-[4-(3-Chloro-4-fluoro-phenyl)-piperazin-1-yl]-2-oxo-acetyl}-3,5-dimethyl-1H-pyrrole-2-carboxylic acid (furan-2-ylmethyl)-amide,
4-{2-[4-(4-Chloro-3-trifluoromethyl-phenyl)-piperazin-1-yl]-2-oxo-acetyl}-3,5-dimethyl-1H-pyrrole-2-carboxylic acid (furan-2-ylmethyl)-amide,
4-{2-[4-(4-Chloro-3-trifluoromethyl-phenyl)-piperazin-1-yl]-2-oxo-acetyl}-3,5-dimethyl-1H-pyrrole-2-carboxylic acid cyclopropylmethyl-amide,
4-{2-[4-(4-Chloro-3-trifluoromethyl-phenyl)-piperazin-1-yl]-2-oxo-acetyl}-3,5-dimethyl-1H-pyrrole-2-carboxylic acid propylamide,
4-{2-[4-(3-Chloro-4-fluoro-phenyl)-piperazin-1-yl]-2-oxo-acetyl}-3,5-dimethyl-1H-pyrrole-2-carboxylic acid cyclopropylmethyl-amide,
4-{2-[4-(3-Chloro-phenyl)-piperazin-1-yl]-2-oxo-acetyl}-3,5-dimethyl-1H-pyrrole-2-carboxylic acid cyclopropylamide,
4-{2-[4-(4-Chloro-3-trifluoromethyl-phenyl)-piperazin-1-yl]-2-oxo-acetyl}-3,5-dimethyl-1H-pyrrole-2-carboxylic acid (pyridin-3-ylmethyl)-amide,
3,5-Dimethyl-4-{2-oxo-2-[4-(3-trifluoromethyl-phenyl)-piperazin-1-yl]-acetyl}-1H-pyrrole-2-carboxylic acid propylamide,
3,5-Dimethyl-4-{2-oxo-2-[4-(3-trifluoromethyl-phenyl)-piperazin-1-yl]-acetyl}-1H-pyrrole-2-carboxylic acid (furan-2-ylmethyl)-amide,
4-{2-[4-(3-Chloro-phenyl)-piperazin-1-yl]-2-oxo-acetyl}-3,5-dimethyl-1H-pyrrole-2-carboxylic acid (furan-2-ylmethyl)-amide,
4-{2-[4-(3-Chloro-phenyl)-piperazin-1-yl]-2-oxo-acetyl}-3,5-dimethyl-1H-pyrrole-2-carboxylic acid cyclopropylmethyl-amide,
1-(4-Bromo-2-methyl-5-phenyl-1H-pyrrol-3-yl)-2-[4-(3-trifluoromethyl-phenyl)-piperazin-1-yl]-ethane-1,2-dione,
(E)-3-(5-Methyl-4-{2-oxo-2-[4-(3-trifluoromethyl-phenyl)-piperazin-1-yl]-acetyl}-2-phenyl-1H-pyrrol-3-yl)-acrylic acid methyl ester, or
(E)-3-(5-Methyl-4-{2-oxo-2-[4-(3-trifluoromethyl-phenyl)-piperazin-1-yl]-acetyl}-2-phenyl-1H-pyrrol-3-yl)-acrylic acid.

6. A process for the preparation of a compound of formula I as claimed in claim 1, which comprises reacting a compound of formula II with a compound of formula III

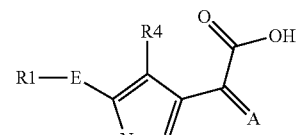

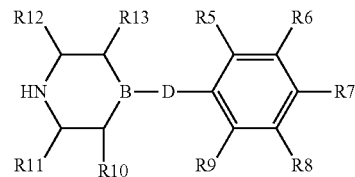

in which the residues R1, R2, R3, R4, R5, R6, R7, R8, R9, R10, R11, R12, R13, A, B, D and E have the meanings indicated in claim 1,
to give a compound of formula I, or
reacting a compound of formula IV with a compound of formula V

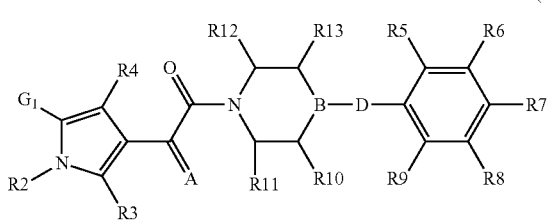

in which the residues R2, R3, R4, R5, R6, R7, R8, R9, R10, R11, R12, R13, A, B and D have the meanings indicated in claim 1, G1 is a carboxylic acid group, and G2 is an amino or hydroxyl group, to give a compound of formula I.

7. A pharmaceutical composition comprising at least one compound as claimed in claim 1, a pharmaceutically acceptable carrier and a fibrinogen-receptor antagonist, a thrombin inhibitor, a factor Xa inhibitor, a heparin, a low-molecular-weight heparin, or aspirin.

8. The pharmaceutical composition of claim 7 wherein the fibrinogen-receptor antagonist is a GP IIb/IIIa monoclonal antibody abciximab (ReoPro), eptifibatide (Integrelin), tirofiban (Aggrastat), roxifiban, lotrafiban, orbofiban, sibrafiban or xemilofiban;

the thrombin inhibitor is ximelagatran, dabigatran or etexilate;

the factor Xa inhibitor is otamixaban, rivaroxaban, apixaban, idraparinux or fondaparinux; and the low-molecular-weight heparin is enoxaparin or dalteparin.

* * * * *